United States Patent
Oster et al.

(10) Patent No.: US 10,155,111 B2
(45) Date of Patent: Dec. 18, 2018

(54) METHODS OF SHIELDING IMPLANTABLE MEDICAL LEADS AND IMPLANTABLE MEDICAL LEAD EXTENSIONS

(71) Applicant: MEDTRONIC, INC., Minneapolis, MN (US)

(72) Inventors: Daniel C. Oster, Minneapolis, MN (US); Jonathan P. Bogott, Crystal, MN (US); Michael J. Schendel, Andover, MN (US); Nathan A. Torgerson, Andover, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 14/807,323

(22) Filed: Jul. 23, 2015

(65) Prior Publication Data

US 2016/0022984 A1   Jan. 28, 2016

Related U.S. Application Data

(60) Provisional application No. 62/028,798, filed on Jul. 24, 2014.

(51) Int. Cl.
*A61N 1/05* (2006.01)
*A61N 1/08* (2006.01)
*A61N 1/37* (2006.01)

(52) U.S. Cl.
CPC ............ *A61N 1/08* (2013.01); *A61N 1/0529* (2013.01); *A61N 1/0553* (2013.01); *A61N 1/3718* (2013.01); *A61N 1/086* (2017.08)

(58) Field of Classification Search
CPC ...... A61N 1/08; A61N 1/0529; A61N 1/0553; A61N 1/3718; A61N 2001/086
(Continued)

(56) References Cited

U.S. PATENT DOCUMENTS 2,433,480 A   12/1947   Rendich
2,487,038 A   11/1949   Jasper
(Continued)

FOREIGN PATENT DOCUMENTS

EP    0617978    10/1994
EP    0624383    11/1994
(Continued)

OTHER PUBLICATIONS

PCT/US2015/014766 International Search Report and Written Opinion, dated Nov. 5, 2015.
(Continued)

*Primary Examiner* — Michael Carey
(74) *Attorney, Agent, or Firm* — Withers & Keys, LLC

(57) ABSTRACT

Shielded sheaths are placed over implantable medical leads and/or implantable medical lead extensions to provide shielding from electromagnetic energy and to prevent heating at the electrodes. The shielded sheaths include insulative bodies with shield layers such as conductive braided wire or conductive foil tubular structures. The shielded sheath may be implanted at the time of implanting the lead and/or lead extension. The shielded sheath may also be implanted at a later time after the lead and/or lead extension has previously been implanted. The shielded sheath may be anchored onto the lead or lead extension.

12 Claims, 32 Drawing Sheets

(58) Field of Classification Search
USPC .................................. 607/116, 36, 37, 132
See application file for complete search history.

(56) References Cited

U.S. PATENT DOCUMENTS

| | | |
|---|---|---|
| 3,788,329 A | 1/1974 | Friedman |
| 3,842,485 A | 10/1974 | Bemert |
| 3,915,174 A | 10/1975 | Preston |
| 4,033,355 A | 7/1977 | Amundson |
| 4,038,990 A | 8/1977 | Thompson |
| 4,214,804 A | 7/1980 | Little |
| 4,220,813 A | 9/1980 | Kyle |
| 4,280,507 A | 7/1981 | Rosenberg |
| 4,320,763 A | 3/1982 | Money |
| 4,350,169 A | 9/1982 | Dutcher |
| 4,383,225 A | 5/1983 | Mayer |
| 4,403,824 A | 9/1983 | Scott |
| 4,411,276 A | 10/1983 | Dickhudt |
| 4,441,498 A | 4/1984 | Nordling |
| 4,628,942 A | 12/1986 | Sweeney et al. |
| 4,683,895 A | 8/1987 | Pohndorf |
| 4,711,027 A | 12/1987 | Harris |
| 4,726,379 A | 2/1988 | Altman et al. |
| 4,852,585 A | 8/1989 | Heath |
| 4,906,241 A | 3/1990 | Noddin |
| 4,920,980 A | 5/1990 | Jackowski |
| 4,922,607 A | 5/1990 | Doan et al. |
| 4,934,380 A | 6/1990 | De Toledo |
| 4,947,866 A | 8/1990 | Lessar et al. |
| 4,951,672 A | 8/1990 | Buchwald et al. |
| 4,991,583 A | 2/1991 | Silvian |
| 5,003,992 A | 4/1991 | Holleman |
| 5,005,587 A | 4/1991 | Scott |
| 5,012,045 A | 4/1991 | Sato |
| 5,018,523 A | 5/1991 | Bach, Jr. et al. |
| 5,020,544 A | 6/1991 | Dahl et al. |
| 5,020,545 A | 6/1991 | Soukup |
| 5,036,862 A | 8/1991 | Pohndorf |
| 5,040,544 A | 8/1991 | Lessar et al. |
| 5,063,932 A | 11/1991 | Dahl et al. |
| 5,197,468 A | 3/1993 | Proctor et al. |
| 5,213,111 A | 5/1993 | Cook et al. |
| 5,217,010 A | 6/1993 | Tsitlik et al. |
| 5,231,078 A | 7/1993 | Riebman et al. |
| 5,243,996 A | 9/1993 | Hall |
| 5,246,438 A | 9/1993 | Langberg |
| 5,260,128 A | 11/1993 | Ishii et al. |
| 5,265,608 A | 11/1993 | Lee et al. |
| 5,265,623 A | 11/1993 | Kroll et al. |
| 5,271,417 A | 12/1993 | Swanson et al. |
| 5,308,664 A | 5/1994 | House et al. |
| 5,314,459 A | 5/1994 | Swanson et al. |
| 5,323,776 A | 6/1994 | Blakely et al. |
| 5,335,657 A | 8/1994 | Terry, Jr. et al. |
| 5,349,133 A | 9/1994 | Rogers |
| 5,360,441 A | 11/1994 | Otten |
| 5,366,496 A | 11/1994 | Dahl et al. |
| 5,370,644 A | 12/1994 | Langberg |
| 5,374,286 A | 12/1994 | Morris |
| 5,374,778 A | 12/1994 | Hashimoto et al. |
| 5,417,719 A | 5/1995 | Hull et al. |
| 5,456,705 A | 10/1995 | Morris |
| 5,458,629 A | 10/1995 | Baudino et al. |
| 5,458,631 A | 10/1995 | Xavier |
| 5,466,252 A | 11/1995 | Soukup et al. |
| 5,473,812 A | 12/1995 | Morris et al. |
| 5,476,496 A | 12/1995 | Strandberg et al. |
| 5,485,667 A | 1/1996 | Kleshinski |
| 5,500,013 A | 3/1996 | Buscemi et al. |
| 5,504,274 A | 4/1996 | McCabe et al. |
| 5,514,172 A | 5/1996 | Mueller |
| 5,515,848 A | 5/1996 | Corbett, III et al. |
| 5,523,534 A | 6/1996 | Meister et al. |
| 5,523,578 A | 6/1996 | Herskovic |
| 5,527,348 A | 6/1996 | Winkler |
| 5,534,018 A | 7/1996 | Wahlstrand |
| 5,552,565 A | 9/1996 | Cartier et al. |
| 5,571,157 A | 11/1996 | McConnell |
| 5,572,594 A | 11/1996 | DeVoe et al. |
| 5,591,218 A | 1/1997 | Jacobson |
| 5,594,304 A | 1/1997 | Graber |
| 5,606,981 A | 3/1997 | Tartacower et al. |
| 5,609,622 A | 3/1997 | Soukup et al. |
| 5,628,780 A | 5/1997 | Helland et al. |
| 5,629,622 A | 5/1997 | Scampini |
| 5,643,254 A | 7/1997 | Scheldrup et al. |
| 5,649,965 A | 7/1997 | Pons et al. |
| 5,662,697 A | 9/1997 | Li et al. |
| 5,676,659 A | 10/1997 | McGurk |
| 5,676,694 A | 10/1997 | Boser et al. |
| 5,683,435 A | 11/1997 | Truex et al. |
| 5,683,444 A | 11/1997 | Huntley et al. |
| 5,697,909 A | 12/1997 | Eggers et al. |
| 5,697,958 A | 12/1997 | Paul et al. |
| 5,702,437 A | 12/1997 | Baudino |
| 5,706,826 A | 1/1998 | Schwager |
| 5,722,998 A | 3/1998 | Prutchi et al. |
| 5,727,552 A | 3/1998 | Ryan |
| 5,751,539 A | 5/1998 | Stevenson et al. |
| 5,766,232 A | 6/1998 | Grevious et al. |
| 5,782,241 A | 7/1998 | Felblinger et al. |
| 5,795,341 A | 8/1998 | Samson |
| 5,807,258 A | 9/1998 | Cimochowski et al. |
| 5,814,076 A | 9/1998 | Brownlee |
| 5,827,997 A | 10/1998 | Chung et al. |
| 5,830,136 A | 11/1998 | Delonzor et al. |
| 5,842,966 A | 12/1998 | Markoll |
| 5,842,986 A | 12/1998 | Avrin et al. |
| 5,851,226 A | 12/1998 | Skubitz et al. |
| 5,897,584 A | 4/1999 | Herman |
| 5,905,627 A | 5/1999 | Brendel et al. |
| 5,927,345 A | 7/1999 | Samson |
| 5,931,861 A | 8/1999 | Werner et al. |
| 5,954,760 A | 9/1999 | Jarl |
| 5,964,705 A | 10/1999 | Truwit et al. |
| 5,968,087 A | 10/1999 | Hess |
| 5,970,429 A | 10/1999 | Martin |
| 5,942,966 A | 12/1999 | Markoll |
| 6,004,269 A | 12/1999 | Crowley |
| 6,016,447 A | 1/2000 | Juran et al. |
| 6,024,703 A | 2/2000 | Zanelli et al. |
| 6,032,063 A | 2/2000 | Hoar et al. |
| 6,033,408 A | 3/2000 | Gage et al. |
| 6,055,457 A | 4/2000 | Bonner |
| 6,101,417 A | 8/2000 | Vogel et al. |
| 6,103,037 A | 8/2000 | Wilson |
| 6,108,582 A | 8/2000 | Fischer, Sr. |
| 6,132,390 A | 10/2000 | Cookston et al. |
| 6,141,593 A | 10/2000 | Patag |
| 6,143,013 A | 11/2000 | Samson et al. |
| 6,152,746 A | 11/2000 | Brown |
| 6,156,029 A | 12/2000 | Mueller |
| 6,195,267 B1 | 2/2001 | MacDonald et al. |
| 6,198,807 B1 | 3/2001 | DeSena |
| 6,198,972 B1 | 3/2001 | Hartlaub et al. |
| 6,209,764 B1 | 4/2001 | Hartlaub et al. |
| 6,240,322 B1 | 5/2001 | Peterfeso |
| 6,258,071 B1 | 7/2001 | Brookes |
| 6,265,466 B1 | 7/2001 | Glatkowski |
| 6,269,148 B1 | 7/2001 | Jessop et al. |
| 6,284,971 B1 | 9/2001 | Atalar et al. |
| 6,302,740 B1 | 10/2001 | Holmstrom |
| 6,348,070 B1 | 2/2002 | Teissl et al. |
| 6,424,234 B1 | 7/2002 | Stevenson |
| 6,471,699 B1 | 10/2002 | Fleischman et al. |
| 6,488,704 B1 | 12/2002 | Connelly et al. |
| 6,494,916 B1 | 12/2002 | Babalola et al. |
| 6,501,991 B1 | 12/2002 | Honeck et al. |
| 6,503,648 B1 | 1/2003 | Wang |
| 6,506,972 B1 | 1/2003 | Wang |
| 6,529,774 B1 | 3/2003 | Greene |
| 6,538,191 B1 | 3/2003 | MacDonald |
| 6,583,361 B2 | 6/2003 | Clouet |
| 6,606,521 B2 | 8/2003 | Paspa et al. |

(56) References Cited

U.S. PATENT DOCUMENTS

| | | |
|---|---|---|
| 6,640,137 B2 | 10/2003 | MacDonald |
| 6,648,690 B2 | 11/2003 | Saito et al. |
| 6,660,116 B2 | 12/2003 | Wolf et al. |
| 6,671,544 B2 | 12/2003 | Baudino |
| 6,671,554 B2 | 12/2003 | Gibson et al. |
| 6,673,999 B1 | 1/2004 | Wang et al. |
| 6,675,033 B1 | 1/2004 | Lardo et al. |
| 6,689,835 B2 | 2/2004 | Amarasekera et al. |
| 6,695,761 B2 | 2/2004 | Oschman et al. |
| 6,708,051 B1 | 3/2004 | Durousseau |
| 6,711,440 B2 | 3/2004 | Deal et al. |
| 6,712,844 B2 | 3/2004 | Pacetti et al. |
| 6,713,671 B1 | 3/2004 | Wang et al. |
| 6,718,203 B2 | 4/2004 | Weiner et al. |
| 6,718,207 B2 | 4/2004 | Connelly |
| 6,725,092 B2 | 4/2004 | MacDonald et al. |
| 6,735,471 B2 | 5/2004 | Hill et al. |
| 6,741,892 B1 | 5/2004 | Meadows et al. |
| 6,743,055 B1 | 6/2004 | Flynn |
| 6,750,055 B1 | 6/2004 | Connelly et al. |
| 6,757,566 B2 | 6/2004 | Weiner et al. |
| 6,760,628 B2 | 7/2004 | Weiner et al. |
| 6,763,268 B2 | 7/2004 | MacDonald et al. |
| 6,765,144 B1 | 7/2004 | Wang et al. |
| 6,768,053 B1 | 7/2004 | Wang et al. |
| 6,778,856 B2 | 8/2004 | Connelly et al. |
| 6,792,316 B2 | 9/2004 | Sass |
| 6,793,642 B2 | 9/2004 | Connelly et al. |
| 6,795,730 B2 | 9/2004 | Connelly et al. |
| 6,795,736 B2 | 9/2004 | Connelly et al. |
| 6,799,067 B2 | 9/2004 | Pacetti |
| 6,799,069 B2 | 9/2004 | Weiner et al. |
| 6,815,609 B1 | 11/2004 | Wang et al. |
| 6,819,954 B2 | 11/2004 | Connelly |
| 6,819,958 B2 | 11/2004 | Weiner et al. |
| 6,844,492 B1 | 1/2005 | Wang et al. |
| 6,845,259 B2 | 1/2005 | Pacetti et al. |
| 6,845,267 B2 | 1/2005 | Harrison et al. |
| 6,846,985 B2 | 1/2005 | Wang et al. |
| 6,850,805 B2 | 2/2005 | Connelly et al. |
| 6,852,091 B2 | 2/2005 | Edwards et al. |
| 6,863,653 B1 | 3/2005 | Zanelli et al. |
| 6,864,418 B2 | 3/2005 | Wang et al. |
| 6,869,683 B2 | 3/2005 | Sakurai et al. |
| 6,871,091 B2 | 3/2005 | Wilkinson et al. |
| 6,872,882 B2 | 3/2005 | Fritz |
| 6,875,180 B2 | 4/2005 | Weiner et al. |
| 6,879,861 B2 | 4/2005 | Benz et al. |
| 6,882,519 B2 | 4/2005 | Uzawa et al. |
| 6,895,280 B2 | 5/2005 | Meadows et al. |
| 6,901,287 B2 | 5/2005 | Davis et al. |
| 6,901,290 B2 | 5/2005 | Foster et al. |
| 6,906,256 B1 | 6/2005 | Wang |
| 6,920,361 B2 | 7/2005 | Williams |
| 6,922,590 B1 | 7/2005 | Whitehurst |
| 6,925,328 B2 | 8/2005 | Foster et al. |
| 6,930,242 B1 | 8/2005 | Helfer |
| 6,937,906 B2 | 8/2005 | Terry et al. |
| 6,944,489 B2 | 9/2005 | Zeiljemaker et al. |
| 6,949,929 B2 | 9/2005 | Gray et al. |
| 6,954,674 B2 | 10/2005 | Connelly |
| 6,968,235 B2 | 11/2005 | Belden et al. |
| 6,968,236 B2 | 11/2005 | Hagele |
| 6,971,391 B1 | 12/2005 | Wang et al. |
| 6,980,865 B1 | 12/2005 | Wang et al. |
| 6,982,378 B2 | 1/2006 | Dickson |
| 6,985,775 B2 | 1/2006 | Reinke et al. |
| 6,993,387 B2 | 1/2006 | Connelly et al. |
| 6,999,818 B2 | 2/2006 | Stevenson et al. |
| 6,999,821 B2 | 2/2006 | Jenney et al. |
| 7,001,369 B2 | 2/2006 | Griffin et al. |
| 7,013,174 B2 | 3/2006 | Connelly et al. |
| 7,013,180 B2 | 3/2006 | Villaseca et al. |
| 7,015,392 B1 | 3/2006 | Dickenson |
| 7,015,393 B2 | 3/2006 | Weiner |
| 7,047,084 B2 | 5/2006 | Erickson |
| 7,050,855 B2 | 5/2006 | Zeijlemaker et al. |
| 7,058,192 B2 | 6/2006 | Muller et al. |
| 7,076,283 B2 | 7/2006 | Cho et al. |
| 7,076,302 B2 | 7/2006 | Scheiner |
| 7,082,328 B2 | 7/2006 | Funke |
| 7,082,337 B2 | 7/2006 | Sommer et al. |
| 7,103,413 B2 | 9/2006 | Swanson |
| 7,113,827 B2 | 9/2006 | Silvestri |
| 7,115,134 B2 | 10/2006 | Chambers |
| 7,118,693 B2 | 10/2006 | Glatkowski et al. |
| 7,123,013 B2 | 10/2006 | Gray |
| 7,125,409 B2 | 10/2006 | Truckai et al. |
| 7,162,302 B2 | 1/2007 | Wang et al. |
| 7,174,219 B2 | 2/2007 | Wahlstrand et al. |
| 7,187,980 B2 | 3/2007 | Osypka et al. |
| 7,233,825 B2 | 6/2007 | Jorgenson et al. |
| 7,257,449 B2 | 8/2007 | Bodner |
| 7,282,260 B2 | 10/2007 | LeGrande et al. |
| 7,286,871 B2 | 10/2007 | Cohen |
| 7,286,882 B2 | 10/2007 | Cole |
| 7,292,894 B2 | 11/2007 | Belden |
| 7,294,785 B2 | 11/2007 | Uutela et al. |
| 7,319,901 B2 | 1/2008 | Dublin |
| 7,363,090 B2 | 4/2008 | Halperin |
| 7,389,148 B1 | 6/2008 | Morgan |
| 7,540,865 B2 | 6/2009 | Griffin et al. |
| 7,548,788 B2 | 6/2009 | Chinn et al. |
| 7,591,831 B2 | 9/2009 | Parsonage et al. |
| 7,674,972 B2 | 3/2010 | Gladd et al. |
| 7,711,436 B2 | 5/2010 | Stone |
| 7,729,777 B2 | 6/2010 | Gray et al. |
| 7,738,942 B2 | 6/2010 | Weiner |
| 7,813,811 B2 | 10/2010 | Wingeier et al. |
| 7,819,826 B2 | 10/2010 | Diederich et al. |
| 7,822,484 B1 | 10/2010 | Zhao et al. |
| 7,828,833 B2 | 11/2010 | Haverkost |
| 7,844,343 B2 | 11/2010 | Wahlstrand |
| 7,844,344 B2 | 11/2010 | Wahlstrand |
| 7,853,332 B2 | 12/2010 | Olsen |
| 7,877,150 B2 | 1/2011 | Hoegh et al. |
| 7,904,178 B2 | 3/2011 | Williams |
| 7,917,213 B2 | 3/2011 | Bulkes |
| 7,933,652 B2 | 4/2011 | Phillips |
| 8,007,440 B2 | 8/2011 | Magnin et al. |
| 8,027,736 B2 | 9/2011 | Wahlstrand |
| 8,036,756 B2 | 10/2011 | Swoyer et al. |
| 8,048,060 B2 | 11/2011 | Griffin et al. |
| 8,055,351 B2 | 11/2011 | Atalar et al. |
| 8,106,657 B2 | 1/2012 | Sakellariou et al. |
| 8,170,691 B2 | 5/2012 | Eckerdal |
| 8,202,259 B2 | 6/2012 | Evans et al. |
| 8,246,643 B2 | 8/2012 | Nita |
| 8,275,464 B2 | 9/2012 | Li et al. |
| 8,280,526 B2 | 10/2012 | Wahlstrand |
| 8,483,842 B2 | 7/2013 | Alexander et al. |
| 8,543,222 B1 | 9/2013 | Sochor |
| 8,620,455 B2 | 12/2013 | Alexander et al. |
| 8,676,340 B2 | 3/2014 | Wahlstrand |
| 8,744,598 B2 | 6/2014 | Alexander et al. |
| 8,788,061 B2 | 7/2014 | Mehdizadeth |
| 8,805,534 B2 | 8/2014 | Olsen |
| 8,903,504 B2 | 12/2014 | Hegland |
| 9,002,474 B2 | 4/2015 | Olsen |
| 9,037,263 B2 | 5/2015 | Marshall |
| 9,044,593 B2 | 6/2015 | Li |
| 2001/0044646 A1 | 11/2001 | Marshall et al. |
| 2002/0032468 A1 | 3/2002 | Hill |
| 2002/0038135 A1 | 3/2002 | Connelly et al. |
| 2002/0058978 A1 | 5/2002 | Sass |
| 2002/0183438 A1 | 5/2002 | Amarasekera et al. |
| 2002/0082673 A1 | 6/2002 | Benz et al. |
| 2002/0106918 A1 | 8/2002 | Saito et al. |
| 2002/0111659 A1 | 8/2002 | Davis et al. |
| 2002/0111663 A1 | 8/2002 | Dahl et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |

(56) References Cited

U.S. PATENT DOCUMENTS

| | | |
|---|---|---|
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0143377 A1 | 10/2002 | Wessman et al. |
| 2002/0183740 A1 | 12/2002 | Edwards et al. |
| 2002/0183822 A1 | 12/2002 | Bodner |
| 2002/0188345 A1 | 12/2002 | Pacetti |
| 2003/0009207 A1 | 1/2003 | Paspa et al. |
| 2003/0014080 A1 | 1/2003 | Baudino |
| 2003/0036776 A1 | 2/2003 | Foster et al. |
| 2003/0044623 A1 | 3/2003 | Sakurai et al. |
| 2003/0045920 A1 | 3/2003 | Belden et al. |
| 2003/0060732 A1 | 3/2003 | Jacobsen et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0093107 A1 | 5/2003 | Parsonage et al. |
| 2003/0109901 A1 | 6/2003 | Greatbatch |
| 2003/0117787 A1 | 6/2003 | Nakauchi |
| 2003/0120148 A1 | 6/2003 | Pacetti |
| 2003/0120197 A1 | 6/2003 | Kaneko et al. |
| 2003/0135114 A1 | 7/2003 | Pacetti et al. |
| 2003/0139794 A1 | 7/2003 | Jenney et al. |
| 2003/0139806 A1 | 7/2003 | Haverkost et al. |
| 2003/0140931 A1 | 7/2003 | Zeijlemaker |
| 2003/0144704 A1 | 7/2003 | Terry |
| 2003/0144705 A1 | 7/2003 | Funke |
| 2003/0144716 A1 | 7/2003 | Reinke et al. |
| 2003/0144717 A1 | 7/2003 | Hegele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0167052 A1 | 9/2003 | Lee et al. |
| 2003/0204217 A1 | 10/2003 | Greatbatch |
| 2003/0225331 A1 | 12/2003 | Diederich et al. |
| 2004/0020674 A1 | 2/2004 | McFadden et al. |
| 2004/0024442 A1 | 2/2004 | Sowinski et al. |
| 2004/0028859 A1 | 2/2004 | LeGrande et al. |
| 2004/0068307 A1 | 4/2004 | Goble |
| 2004/0071949 A1 | 4/2004 | Glatkowski et al. |
| 2004/0088012 A1 | 5/2004 | Kroll et al. |
| 2004/0106958 A1 | 6/2004 | Mathis et al. |
| 2004/0162600 A1 | 8/2004 | Williams |
| 2004/0167443 A1 | 8/2004 | Shireman et al. |
| 2004/0173368 A1 | 9/2004 | Dickson |
| 2004/0199069 A1 | 10/2004 | Connelly et al. |
| 2004/0220549 A1 | 11/2004 | Dittman et al. |
| 2004/0249428 A1 | 12/2004 | Wang et al. |
| 2004/0251042 A1 | 12/2004 | Weiner et al. |
| 2004/0263172 A1 | 12/2004 | Gray et al. |
| 2004/0263173 A1 | 12/2004 | Gray |
| 2004/0263174 A1 | 12/2004 | Gray et al. |
| 2004/0267328 A1 | 12/2004 | Duffin |
| 2005/0065587 A1 | 3/2005 | Gryzwa |
| 2005/0070972 A1 | 3/2005 | Wahlstrand |
| 2005/0080471 A1 | 4/2005 | Chitre et al. |
| 2005/0113876 A1 | 5/2005 | Weiner |
| 2005/0115624 A1 | 6/2005 | Walak |
| 2005/0137664 A1 | 6/2005 | Sommer et al. |
| 2005/0145307 A1 | 7/2005 | Shireman et al. |
| 2005/0159661 A1 | 7/2005 | Connelly et al. |
| 2005/0182471 A1 | 8/2005 | Wang |
| 2005/0222642 A1 | 10/2005 | Przybyszewski |
| 2005/0222647 A1 | 10/2005 | Wahlstrand |
| 2005/0222656 A1 | 10/2005 | Wahlstrand |
| 2005/0222657 A1 | 10/2005 | Wahlstrand |
| 2005/0222658 A1 | 10/2005 | Hoegh et al. |
| 2005/0222659 A1 | 10/2005 | Olsen |
| 2006/0030918 A1 | 2/2006 | Chinn et al. |
| 2006/0036306 A1 | 2/2006 | Heist et al. |
| 2006/0079926 A1 | 4/2006 | Desai et al. |
| 2006/0089680 A1 | 4/2006 | Bruchmann et al. |
| 2006/0095078 A1 | 5/2006 | Tronnes |
| 2006/0135962 A1 | 6/2006 | Kick et al. |
| 2006/0155270 A1 | 7/2006 | Hancock |
| 2006/0167522 A1 | 7/2006 | Malinowski |
| 2006/0167527 A1 | 7/2006 | Malinowski |
| 2006/0200218 A1 | 9/2006 | Wahlstrand |
| 2006/0224207 A1 | 10/2006 | Dublin |
| 2006/0247747 A1 | 11/2006 | Olsen |
| 2006/0247748 A1 | 11/2006 | Wahlstrand |
| 2007/0021811 A1 | 1/2007 | D'Aquanni et al. |
| 2007/0106332 A1 | 5/2007 | Denker |
| 2007/0123805 A1 | 5/2007 | Shireman et al. |
| 2007/0129779 A1 | 6/2007 | Ayre |
| 2007/0168008 A1 | 7/2007 | Olsen |
| 2007/0185556 A1 | 8/2007 | Williams |
| 2007/0208383 A1 | 9/2007 | Williams |
| 2007/0293924 A1 | 12/2007 | Belden et al. |
| 2008/0033497 A1 | 2/2008 | Bulkes |
| 2008/0039709 A1 | 2/2008 | Karmarkar |
| 2008/0058715 A1 | 3/2008 | Houser et al. |
| 2008/0154326 A1 | 6/2008 | Clyne |
| 2008/0183263 A1 | 7/2008 | Alexander |
| 2008/0195186 A1 | 8/2008 | Li |
| 2008/0195187 A1 | 8/2008 | Li |
| 2008/0215008 A1 | 9/2008 | Nance et al. |
| 2008/0242944 A1 | 10/2008 | Sharma |
| 2008/0243081 A1 | 10/2008 | Nance et al. |
| 2008/0243218 A1 | 10/2008 | Bottomley |
| 2008/0262582 A1 | 10/2008 | Alexander |
| 2008/0262584 A1* | 10/2008 | Bottomley ............... A61N 1/05 607/119 |
| 2008/0269863 A1 | 10/2008 | Alexander |
| 2008/0287804 A1 | 11/2008 | Nita |
| 2009/0171421 A1 | 7/2009 | Atalar et al. |
| 2009/0204192 A1 | 8/2009 | Carlton |
| 2009/0221970 A1 | 9/2009 | Spinoza |
| 2009/0228074 A1 | 9/2009 | Edgell et al. |
| 2009/0234402 A1 | 9/2009 | Marshall |
| 2009/0240235 A1 | 9/2009 | Murata |
| 2009/0259272 A1 | 10/2009 | Reddy |
| 2009/0270956 A1 | 10/2009 | Vase |
| 2009/0287189 A1 | 11/2009 | Suwito |
| 2010/0036466 A1 | 2/2010 | Min |
| 2010/0069743 A1 | 3/2010 | Sheetz et al. |
| 2010/0100164 A1 | 4/2010 | Johnson et al. |
| 2010/0137957 A1 | 6/2010 | Eckerdal |
| 2010/0145426 A1 | 6/2010 | Stone |
| 2010/0198327 A1 | 8/2010 | Helland |
| 2010/0256528 A1 | 10/2010 | Lippert et al. |
| 2010/0256604 A1 | 10/2010 | Lippert et al. |
| 2010/0256696 A1 | 10/2010 | Schleicher et al. |
| 2010/0268310 A1 | 10/2010 | Bonde et al. |
| 2010/0331938 A1* | 12/2010 | Sommer ............... A61N 1/0534 607/116 |
| 2011/0015713 A1 | 1/2011 | Min |
| 2011/0034983 A1 | 2/2011 | Min |
| 2011/0071599 A1 | 3/2011 | Olsen |
| 2011/0071604 A1 | 3/2011 | Wahlstrand |
| 2011/0071605 A1 | 3/2011 | Wahlstrand |
| 2011/0112615 A1 | 5/2011 | Hoegh et al. |
| 2011/0230943 A1 | 9/2011 | Johnson et al. |
| 2011/0251487 A1 | 10/2011 | Magnin et al. |
| 2011/0319905 A1 | 12/2011 | Palme et al. |
| 2012/0010689 A1 | 1/2012 | Wahlstrand |
| 2012/0035616 A1 | 2/2012 | Olsen et al. |
| 2012/0035694 A1 | 2/2012 | Olsen |
| 2012/0035695 A1 | 2/2012 | Olsen et al. |
| 2012/0035696 A1 | 2/2012 | Kern |
| 2012/0035697 A1 | 2/2012 | Stone |

(56) References Cited

U.S. PATENT DOCUMENTS

| | | |
|---|---|---|
| 2012/0035951 A1 | 2/2012 | Goetz |
| 2012/0041528 A1 | 2/2012 | Mehdizadeh et al. |
| 2012/0041529 A1 | 2/2012 | Olsen |
| 2012/0046722 A1* | 2/2012 | Olsen ............... A61N 1/3718 607/116 |
| 2012/0053664 A1 | 3/2012 | Hegland |
| 2012/0059467 A1 | 3/2012 | Drew |
| 2012/0130461 A1 | 5/2012 | Olsen |
| 2012/0283835 A1* | 11/2012 | Bentley ............. A61N 1/0558 623/17.16 |
| 2012/0330383 A1 | 12/2012 | Wahlstrand |
| 2013/0296991 A1 | 11/2013 | Alexander et al. |
| 2013/0317518 A1 | 11/2013 | Govea |
| 2014/0107746 A1 | 4/2014 | Alexander et al. |
| 2014/0200643 A1 | 7/2014 | Wahlstrand |
| 2014/0288626 A1 | 9/2014 | Alexander et al. |
| 2014/0345132 A1 | 11/2014 | Mehdizadeh et al. |
| 2014/0350654 A1 | 11/2014 | Olsen et al. |
| 2015/0082618 A1 | 3/2015 | Hegland |
| 2015/0170792 A1 | 6/2015 | Alford |
| 2015/0374977 A1* | 12/2015 | Howard ............. A61N 1/08 607/119 |

FOREIGN PATENT DOCUMENTS

| | | |
|---|---|---|
| EP | 0713714 | 5/1996 |
| EP | 0760196 | 3/1997 |
| EP | 0920239 | 6/1999 |
| EP | 1273922 | 1/2003 |
| EP | 1424095 | 6/2004 |
| EP | 1466576 | 10/2004 |
| EP | 1625875 | 2/2006 |
| EP | 1632265 | 3/2006 |
| EP | 1935449 | 6/2008 |
| GB | 2429154 | 2/2007 |
| JP | 07/255863 | 10/1995 |
| JP | 11/086641 | 3/1999 |
| WO | WO95/032673 | 12/1995 |
| WO | WO96/016694 | 6/1996 |
| WO | WO96/028951 | 9/1996 |
| WO | WO97/041923 | 11/1997 |
| WO | WO98/048896 | 11/1998 |
| WO | WO99/010035 | 3/1999 |
| WO | WO99/019020 | 4/1999 |
| WO | WO99/060370 | 11/1999 |
| WO | WO00/027279 | 5/2000 |
| WO | WO01/080940 | 11/2001 |
| WO | WO02/000292 | 1/2002 |
| WO | WO02/083236 | 10/2002 |
| WO | WO03/037429 | 5/2003 |
| WO | WO03/061755 | 7/2003 |
| WO | WO03/063946 | 8/2003 |
| WO | WO03/063948 | 8/2003 |
| WO | WO03/063952 | 8/2003 |
| WO | WO03/063953 | 8/2003 |
| WO | WO03/063954 | 8/2003 |
| WO | WO03/063955 | 8/2003 |
| WO | WO03/063956 | 8/2003 |
| WO | WO03/063957 | 8/2003 |
| WO | WO03/075797 | 9/2003 |
| WO | WO03/092326 | 11/2003 |
| WO | WO03/095022 | 11/2003 |
| WO | WO04/012809 | 2/2004 |
| WO | WO04/052448 | 6/2004 |
| WO | WO04/073040 | 8/2004 |
| WO | WO05/030322 | 4/2005 |
| WO | WO05/032654 | 4/2005 |
| WO | WO05/102444 | 11/2005 |
| WO | WO05/102445 | 11/2005 |
| WO | WO05/102446 | 11/2005 |
| WO | WO05/102447 | 11/2005 |
| WO | WO06/031317 | 3/2006 |
| WO | WO06/093685 | 9/2006 |
| WO | WO06/093686 | 9/2006 |
| WO | WO06/118640 | 11/2006 |
| WO | WO06/118641 | 11/2006 |
| WO | WO07/047966 | 4/2007 |
| WO | WO07/124273 | 11/2007 |
| WO | WO07/126657 | 11/2007 |
| WO | WO07/149757 | 12/2007 |
| WO | WO08/100840 | 2/2008 |
| WO | WO08/088568 | 7/2008 |
| WO | WO08/100839 | 8/2008 |
| WO | WO08/111986 | 9/2008 |
| WO | WO08/130409 | 10/2008 |
| WO | WO08/134196 | 11/2008 |
| WO | WO08/140376 | 11/2008 |
| WO | WO09/011440 | 9/2009 |
| WO | WO09/134901 | 11/2009 |
| WO | WO10/062988 | 6/2010 |
| WO | WO10/126871 | 11/2010 |
| WO | WO10/126877 | 11/2010 |
| WO | WO10/126884 | 11/2010 |
| WO | WO10/126887 | 11/2010 |
| WO | WO10/126935 | 11/2010 |
| WO | WO10/126939 | 11/2010 |
| WO | WO10/126943 | 11/2010 |
| WO | WO10/126946 | 11/2010 |
| WO | WO10/126949 | 11/2010 |
| WO | WO10/126975 | 11/2010 |
| WO | WO10/135440 | 11/2010 |
| WO | WO11/019416 | 2/2011 |
| WO | WO12/103419 | 8/2012 |
| WO | WO13/158189 | 10/2013 |

OTHER PUBLICATIONS

PCT/US2004/042081: Search Report and Written Opinion.
PCT/US2005/000322: Search Report and Written Opinion.
PCT/US2008/053540: Search Report and Written Opinion.
PCT/US2008/053541: Search Report and Written Opinion.
PCT/US2008/059358: Search Report and Written Opinion.
PCT/US2009/036461: Search Report and Written Opinion.
PCT/US2010/032516: Search Report and Written Opinion.
PCT/US2010/032526: Search Report and Written Opinion.
PCT/US2010/032543: Search Report and Written Opinion.
PCT/US2010/032560: Search Report and Written Opinion.
PCT/US2010/032567: Search Report and Written Opinion.
PCT/US2010/032666: Search Report and Written Opinion.
PCT/US2010/032671: Search Report and Written Opinion.
PCT/US2010/032675: Search Report and Written Opinion.
PCT/US2010/032682: Search Report and Written Opinion.
PCT/US2010/032719: Search Report and Written Opinion.
PCT/US2013/023637: Search Report and Written Opinion.
Baker et al., "Evaluation of Specific Absorption Rates as a Dosimeter of MRI-Related Implant Heating", Journal of Magnetic Resonance Imaging 20:315-320 (2004).
Baker, K., et al., "Neurostimulation Systems: Assessment of Magnetic Field Interactions Associated with 1.5 and 3-Tesla MR Systems", J. Magn. Reson. Imaging, Jan. 2005, 21(1);72-7.
Chung, D.D.L., "Carbon Fiber Composites", 1994, chapter 1, p. 8, table 1.2, Elsevier, ISBN: 978-0-7506-9169-7.
Chung, D.D.L., Comparison of Submicron-Diameter Carbon Filaments and Conventional Carbon Fibers as Fillers in Composite Materials, Carbon 39 (2001) pp. 1119-1125, Elsevier Science Ltd.
Chung, D.D.L., Electromagnetic Interference Shielding Effectiveness of Carbon Materials, Carbon 29 (2001) pp. 279-285, Elsevier Science Ltd.
Engdahl, Tomi, "Ground Loop Basics." Web Jan. 4, 2009, ePanorama. net www.epanorama.net/documents/groundloop/basics.html 28052. 00 U.S. Appl. No. 11/739,787.
Finelli, D., et al., "MRI Imaging-Related Heating of Deep Brain Stimulation Electrodes: In Vitro Study", AJNR AM. J. Neuroadiol 23:1, Nov./Dec. 2002.
Jou, W.S. "A Novel Structure of Woven Continuous-Carbon Fiber Composites with High Electromagnetic Shielding", Journal of Electronic Materials, vol. 33, No. 3, Mar. 1, 2004, pp. 162-170(9), Minerals, Metals and Materials Society, http://findarticles.com/p/articles/mi_au3776/is_200403/ai_n9405_582/print.

(56) References Cited

OTHER PUBLICATIONS

Kolin, et al., "An Electromagnetic Catheter Flow Meter for Determination of Blood Flow in Major Arteries," Department of Biophysics, Physiology, and Radiology, University of California School of Medicine (Los Angeles) Jan. 19, 1988, Proc. N.A.S. vol. 59, pp. 808-815.

Kolin, et al., "An Electromagnetic Intravascular Blood-Flow Sensor", Department of Biophysics, University of California School of Medicine (Los Angeles), Mar. 20, 1967, Proc. N.A.S., vol. 57, pp. 1331-1337.

Kolin, et al., "Miniaturization of the Electromagnetic Blood Flow Meter and Its Use for the Recording of Circulatory Responses of Conscious Animals to Sensory Stimuli", Department of Biophysics, University of California at Los Angeles, Aug. 1959, Proc. N.A.S. vol. 45(8), pp. 1312-1321.

Medtronic Activa Product Family and Procedure Solution Brochure, Medtronic, Inc, 2001.

Medtronic Neurostimulation Systems Brochure, Medtronic, Inc., 2002.

Quick et al., "Endourethral MRI", Magnetic Resonance in Medicine, 45:138-146, 2001.

Rezai, A., et al., "Neurostimulation System Used for Deep Brain Stimulation (DBS): MR Safety Issues and Implications of Failing to Follow Safety Recommendations" Investigative Radiology, May 2004, vol. 39, Issue 5, pp. 300-303.

Rezai, A., et al., "Neurostimulation Systems for Deep Brain Stimulation In Vitro Evaluation of Magnetic Resonance Imaging-Related Healing at 1.5 Tesla", Journal of Magnetic Reson. Imaging 2002; 15:241-50.

U.S. Appl. No. 14/804,020, filed Jul. 20, 2015.
U.S. Appl. No. 14/804,020, Restriction Requirement, dated Apr. 20, 2016.
U.S. Appl. No. 14/804,020, Response filed Jun. 20, 2016.
U.S. Appl. No. 14/804,020 Non-Final Office Action dated Jul. 5, 2016.
U.S. Appl. No. 14/804,020, Response Filed Oct. 5, 2016.
U.S. Appl. No. 14/804,020, Non-Final Office Action dated Feb. 1, 2017.
U.S. Appl. No. 14/804,020, Response filed May 1, 2017.
U.S. Appl. No. 14/804,020, Final Office Action dated Jun. 26, 2017.
U.S. Appl. No. 14/804,020, Response filed Aug. 26, 2017.
U.S. Appl. No. 14/804,020, Advisory Action, dated Sep. 29, 2017.
U.S. Appl. No. 14/804,020, Response-Rce Request filed Sep. 25, 2017.
European Application No. 15 745 714.4-1124, EP Office Action Communication, dated Oct. 8, 2018.

\* cited by examiner

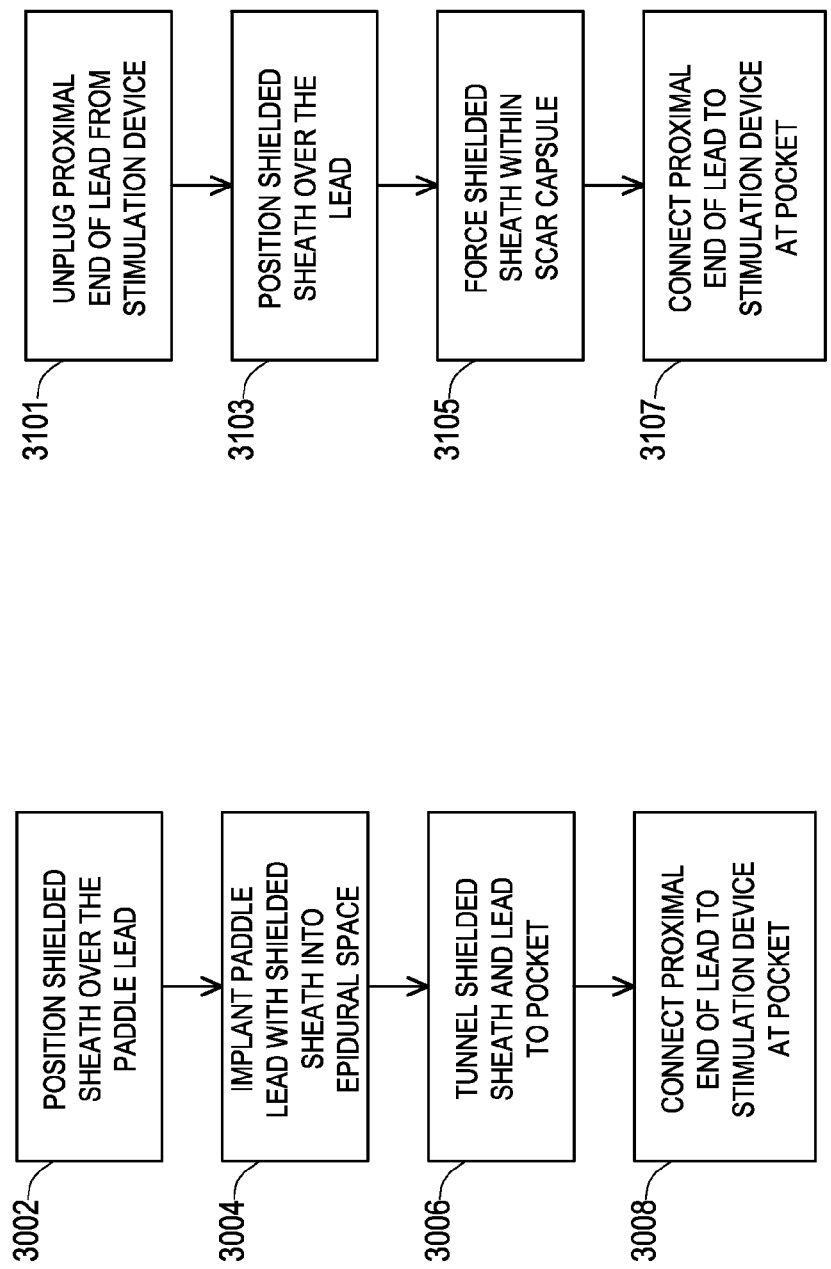

METHODS OF SHIELDING IMPLANTABLE MEDICAL LEADS AND IMPLANTABLE MEDICAL LEAD EXTENSIONS

RELATED APPLICATIONS

The present application claims priority to U.S. Provisional Application No. 62/028,798, filed Jul. 24, 2014, which is incorporated herein in its entirety.

TECHNICAL FIELD

Embodiments relate to implantable medical leads and implantable medical lead extensions. More particularly, embodiments relate to methods of shielding implantable medical leads and implantable medical lead extensions.

BACKGROUND

Implantable medical systems are used to provide stimulation therapy and/or physiological sensing for patients. The implantable medical system includes a stimulation or sensing device that is implanted at a convenient location. Implantable medical leads are routed between the site of implantation of the device and a target site where stimulation or sensing is to occur. Where the route is lengthy, an implantable medical lead extension is used to traverse a portion of that distance.

The implantable medical leads include one or more electrical contacts located near a proximal end of the lead. Where no extension is needed, the proximal end of the lead is physically connected to the stimulation or sensing device so that the proximal contacts of the lead are electrically coupled to electrical circuitry of the device. For scenarios where the implantable medical lead extension is used, then the proximal end of the lead is physically connected to a distal end of the extension where electrical connectors of the extension are coupled to the electrical contacts of the lead. The proximal end of the extension is physically connected to the stimulation or sensing device so that the proximal contacts of the extension are electrically coupled to electrical circuitry of the device. The leads also include one or more electrodes located near a distal end of the leads. Electrical conductors are present within the lead, and each electrical conductor is connected to a respective electrical contact and electrode to provide an electrical path for stimulation and/or sensed signals. Electrical conductors are also present within the extension, and each electrical conductor is connected to a respective electrical contact and distal connector to provide an electrical path for stimulation and/or sensed signals.

Because the lead and lead-extension combination extends over a significant distance within the body, each electrical conductor within the lead and extension is susceptible to receiving extraneous electromagnetic energy that produces electrical current on the electrical conductor. While most ambient conditions expose the lead and lead extension to insignificant levels of such extraneous electromagnetic energy, certain situations may create levels of extraneous electromagnetic energy that are of concern. An example of such a situation is a magnetic resonance imaging (MRI) scan. The MRI scan utilizes a high energy radio frequency (RF) electromagnetic signal. This RF signal may produce relatively large levels of electrical current on the electrical conductor of the lead and extension when the patient having the implantable medical system that includes the lead and/or lead extension combination undergoes the MRI scan. The relatively large electrical current that results from the high energy RF signal produces heating at the electrodes that may create discomfort and even dangerous tissue damage at the site within the body where the one or more electrodes of the lead are located.

It has been found that a shield layer within the lead reduces the amount of RF energy that reaches the electrical conductors, which in turn reduces the amount of current being coupled onto the electrical conductors and reduces the heating at the electrodes to acceptable levels. The manufacturing process of the lead has been altered to include a shield layer when the lead body is being manufactured by creating an inner jacket over the electrical conductor, then creating the shield layer on the inner jacket, and then creating an outer jacket over the inner jacket. The electrical contacts and electrodes are then installed about the inner jacket and are coupled to the electrical conductor to complete the leads. However, leads and extensions that have been constructed without such shield layers or other protective aspects remain vulnerable to the high levels of RF energy of the MRI scan or other situation.

Additionally, patients having leads and/or extensions implanted that are not designed to be safe during an MRI scan either continue to be ineligible for an MRI scan or must undergo a procedure to replace the lead and/or extension with an MRI compliant version. Replacing the existing lead presents a risk that the new lead will not be positioned in a location that provides therapy that is as effective as with the prior lead. Furthermore, some leads are very difficult to remove, such as leads having a distal paddle that have required surgical procedures for implantation.

SUMMARY

Embodiments address issues such as these and others by adding a shielded sheath over an existing lead or extension. The shielded sheath may then be anchored to the existing lead or extension and to the surrounding body tissue. The shielded sheath may be added to newly implanted leads and/or extensions or to leads and/or extensions that have previously been implanted.

Embodiments provide a method of shielding an implantable medical lead. The method involves providing a sheath that includes a shield layer. The method further involves positioning the sheath that includes the shield layer about an implantable medical lead between a proximal contact on the implantable medical lead and a distal electrode on the implantable medical lead. The method additionally involves anchoring the sheath to the implantable medical lead.

Embodiments provide an apparatus that includes an implantable medical lead having a proximal contact and a distal electrode and also includes a sheath containing a shield layer positioned about the implantable medical lead between the proximal contact and the distal electrode. The apparatus further includes an anchoring structure holding the sheath in a fixed position about the implantable medical lead.

Embodiments provide an implantable medical system that includes an implantable stimulation device and an implantable medical lead having a proximal contact and a distal electrode with the proximal contact being electrically coupled to the implantable stimulation device. The system further includes a sheath containing a shield layer positioned about the implantable medical lead between the proximal contact and the distal electrode and an anchoring structure holding the sheath in a fixed position about the implantable medical lead.

Embodiments provide an apparatus that includes an implantable medical lead extension having a proximal contact and a distal connector block and also includes a sheath containing a shield layer positioned about the implantable medical lead between the proximal contact and a distal end of the implantable medical lead extension. The apparatus further includes an anchoring structure holding the sheath in a fixed position about the implantable medical lead extension.

Embodiments provide a method of shielding an implantable medical paddle lead that involves providing a sheath that includes a shield layer. The method further involves positioning the sheath that includes the shield layer about an implantable medical lead between a proximal contact on the implantable medical lead and a paddle portion of the implantable medical paddle lead, the sheath having an inner diameter that is smaller than a width of the paddle portion of the paddle lead but greater than a diameter of a remainder of the paddle lead such that the sheath is confined by the paddle portion.

Embodiments provide an apparatus that includes an implantable medical paddle lead having a proximal contact and a paddle portion that contains at least one distal electrode, the paddle portion having a width greater than a remainder of the implantable medical paddle lead. The apparatus further includes a sheath containing a shield layer positioned about the implantable medical lead between the proximal contact and the paddle portion, the sheath having an inner diameter that is smaller than a width of the paddle portion of the paddle lead but greater than a diameter of a remainder of the paddle lead such that the sheath is confined by the paddle portion.

Embodiments provide an implantable medical system that includes an implantable stimulation device. The system further includes an implantable medical paddle lead having a proximal contact and a paddle portion that contains at least one distal electrode with the proximal contact being electrically coupled to the implantable stimulation device, the paddle portion having a width greater than a remainder of the implantable medical paddle lead. The system additionally includes a sheath containing a shield layer positioned about the implantable medical lead between the proximal contact and the paddle portion, the sheath having an inner diameter that is smaller than a width of the paddle portion of the paddle lead but greater than a diameter of a remainder of the paddle lead such that the sheath is confined by the paddle portion.

DESCRIPTION OF THE DRAWINGS

FIG. 30 shows a set of operations for another manner of implanting a shielded sheath and an implantable medical paddle lead.

FIGS. 31A and 31B show sets of operations for ways of implanting a shielded sheath onto a previously implanted medical paddle lead.

DETAILED DESCRIPTION

Embodiments provide shielded sheaths that are installed over leads and/or extensions, whether being implanted or already implanted. The shielded sheath reduces the amount of RF energy that reaches the conductors of the lead and/or extension.

Figure 1:
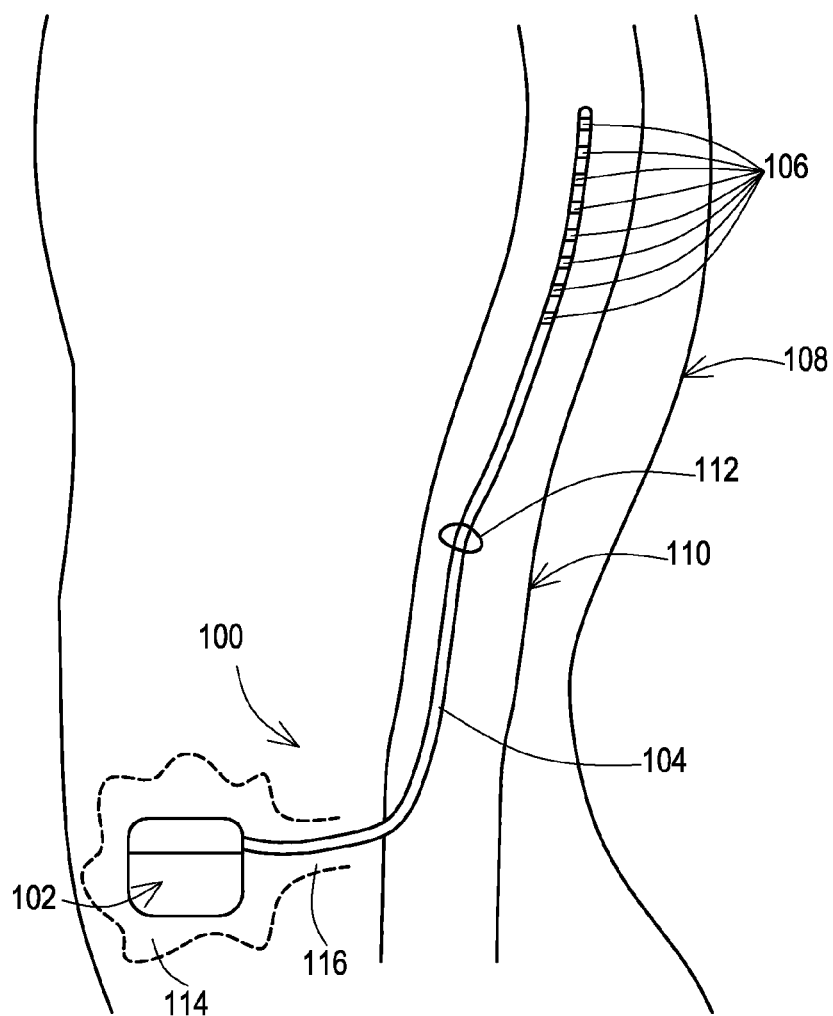
FIG. 1 shows an implantable medical system including a lead that has been implanted prior to introduction of a shielded sheath.

FIG. 1 shows an example where a shielded sheath may be utilized. An implantable medical system 100 that includes an implantable medical device 102 which may be an implantable stimulation device that provides electrical stimulation signals and/or senses physiological signals. The system 100 also includes an implantable medical lead 104 is implanted into a patient 108. In this particular example, the implantable medical system is a spinal cord stimulator where the lead 104 is implanted into a location nearby the spinal cord within the spine 110. The implantable medical device 102 provides electrical stimulation that is delivered through conductors of the lead 104 to the stimulation site. The implantable medical device 102 is implanted within a subcutaneous pocket 114 created during implantation while the lead 104 is tunneled through a path 116 created between the pocket 114 and the entry point 112 to an epidural space during implantation.

Figure 2:
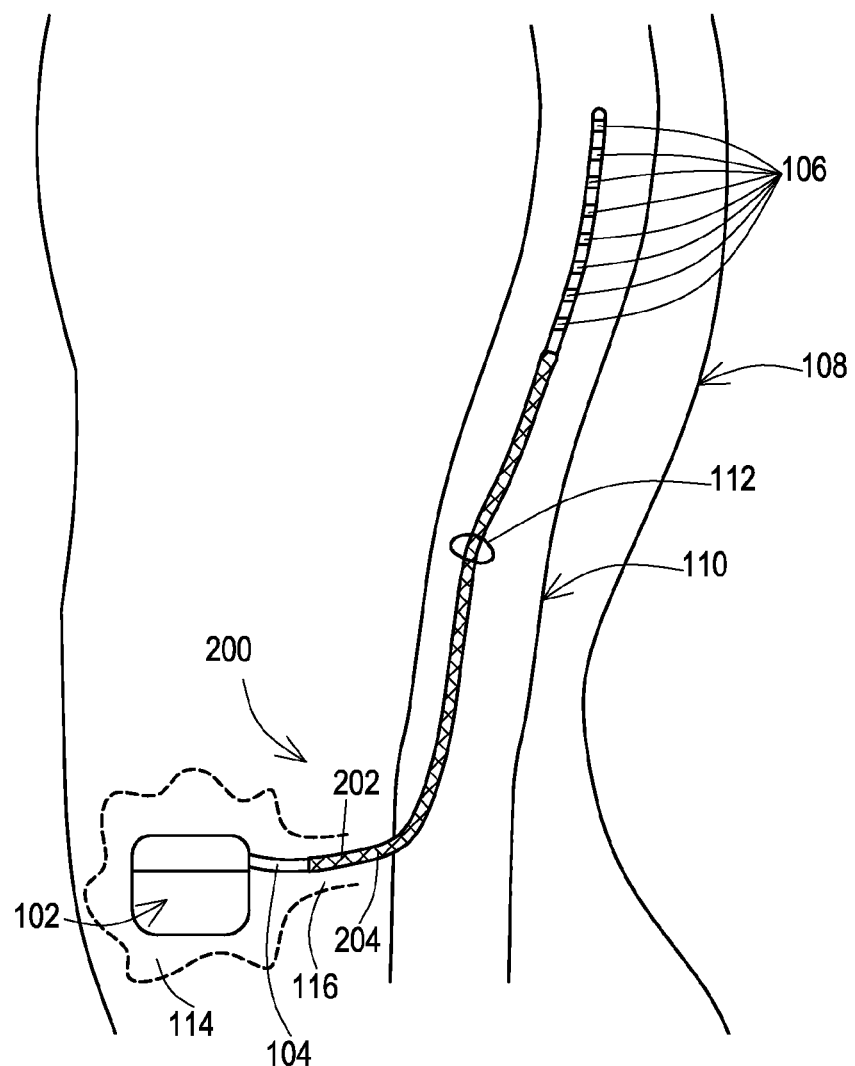
FIG. 2 shows the implantable medical system with the shielded sheath installed over the lead.

FIG. 2 shows an implantable medical system 200 which is identical to the system 100 of FIG. 1 except that a shielded sheath 202 has been placed over the lead 104. The shielded sheath is positioned between the proximal end where the lead 104 connects to the implantable medical device and the distal end where the electrodes 106 are located. The shielded sheath 202 has an insulative shield body with a shield layer 204 within the shield body to isolate the shield layer 204 from the external conditions of the body 108. The shielded sheath provides shielding of RF electromagnetic energy to reduce the amount of RF electromagnetic energy that becomes coupled to the conductors that are within the lead 104 and are connected between the implantable medical device 102 and the electrodes 106.

Figure 26:
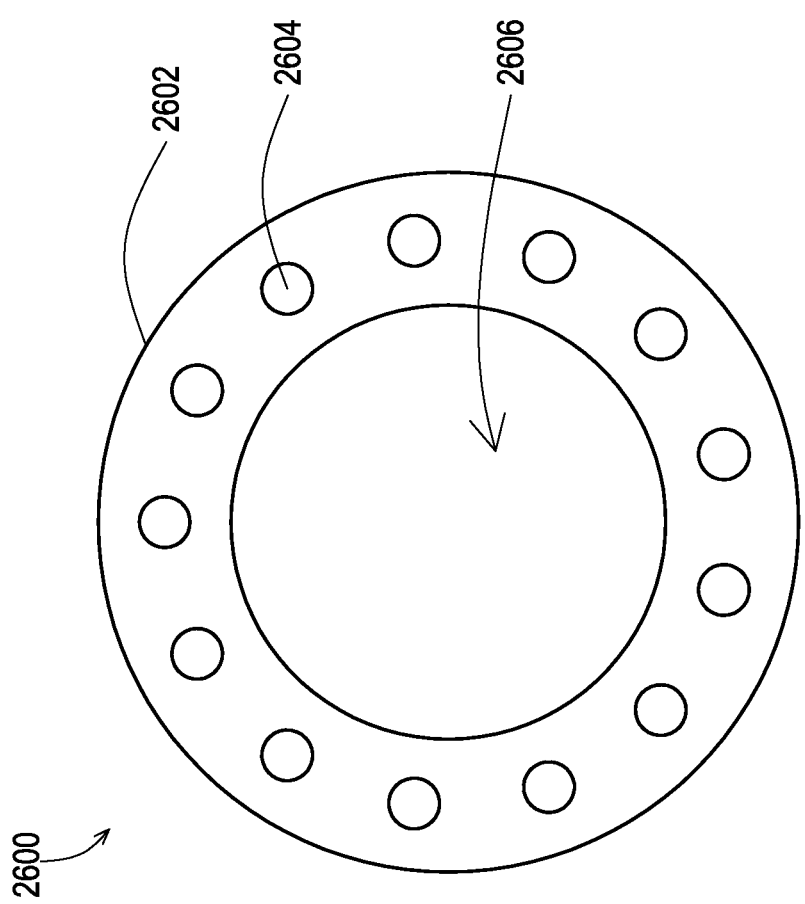
FIG. 26 shows a lateral cross-sectional view of an example of a shielded sheath.

FIG. 26 shows a lateral cross-sectional view of an example 2600 of the shielded sheath 202. In the shielded sheath 2600, there is an insulative shield body 2602 that defines a lumen 2606 where the lead 104 or a lead extension may pass through. The insulative body may be constructed of various biocompatible materials including various polymers, urethanes such as the PurSil® thermoplastic silicone-polyether-urethane of the Koninklijke DSM N.V. Corporation of the Netherlands, and other silicones. A shield layer 2604 is also present and is embedded within the insulative layer. The shield layer 204 in FIG. 2 as well as the shield layer 2604 of FIG. 26 is in the form of a tubular structure of braided conductive wires to provide a tubular braided shield layer. However, other forms of shield layers are also possible, for instance, a conductive foil tube. For a braided shield, the wires of the braid may be a conductor such as a biocompatible metal like tantalum, titanium, and the like. For a foil shield, the foil may be a conductor such as a biocompatible metal like titanium, tantalum, stainless steel, MP35N® alloy of SPS Technologies, Inc. of Jenkintown, Pa., and the like.

Where the shield layer 204 is a braided wire shield as shown in FIG. 2, the braid may be created with a variety of shield parameters. Examples of shield parameters such as braid angle, wire cross-sectional shape and diameter, number of braid wires, braid depth, distance from shield termination to closest contact or electrode, and the like that may also be used for the embodiments being disclosed herein are described in U.S. patent application Ser. No. 13/264,067, which is incorporated herein by reference in its entirety.

The shielded sheath 202 may be installed during a new implantation of the lead 104 or as a retrofit to a lead 104 that has previously been implanted. Examples of procedures for installing the shielded sheath 202 are discussed below, with the procedure for installing during a new spinal implantation of the lead 104 being described with reference to FIGS. 3-11 and the procedure for retrofitting a spinal lead 104 that has previously been implanted with reference to FIGS. 12-17. An example of a procedure for installing the shielded sheath for a brain lead is discussed below in relation to FIGS. 18-23.

Figure 3:
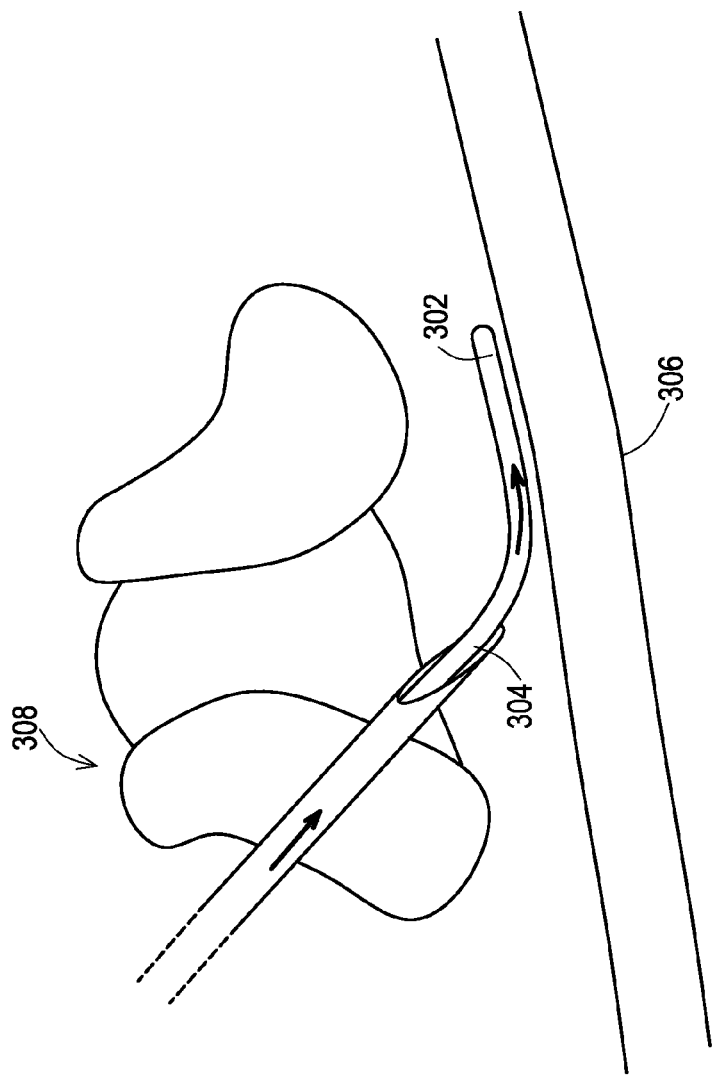
FIG. 3 shows an example of a procedure that begins with a needle being inserted into an epidural space followed by a guidewire.
Figure 11:
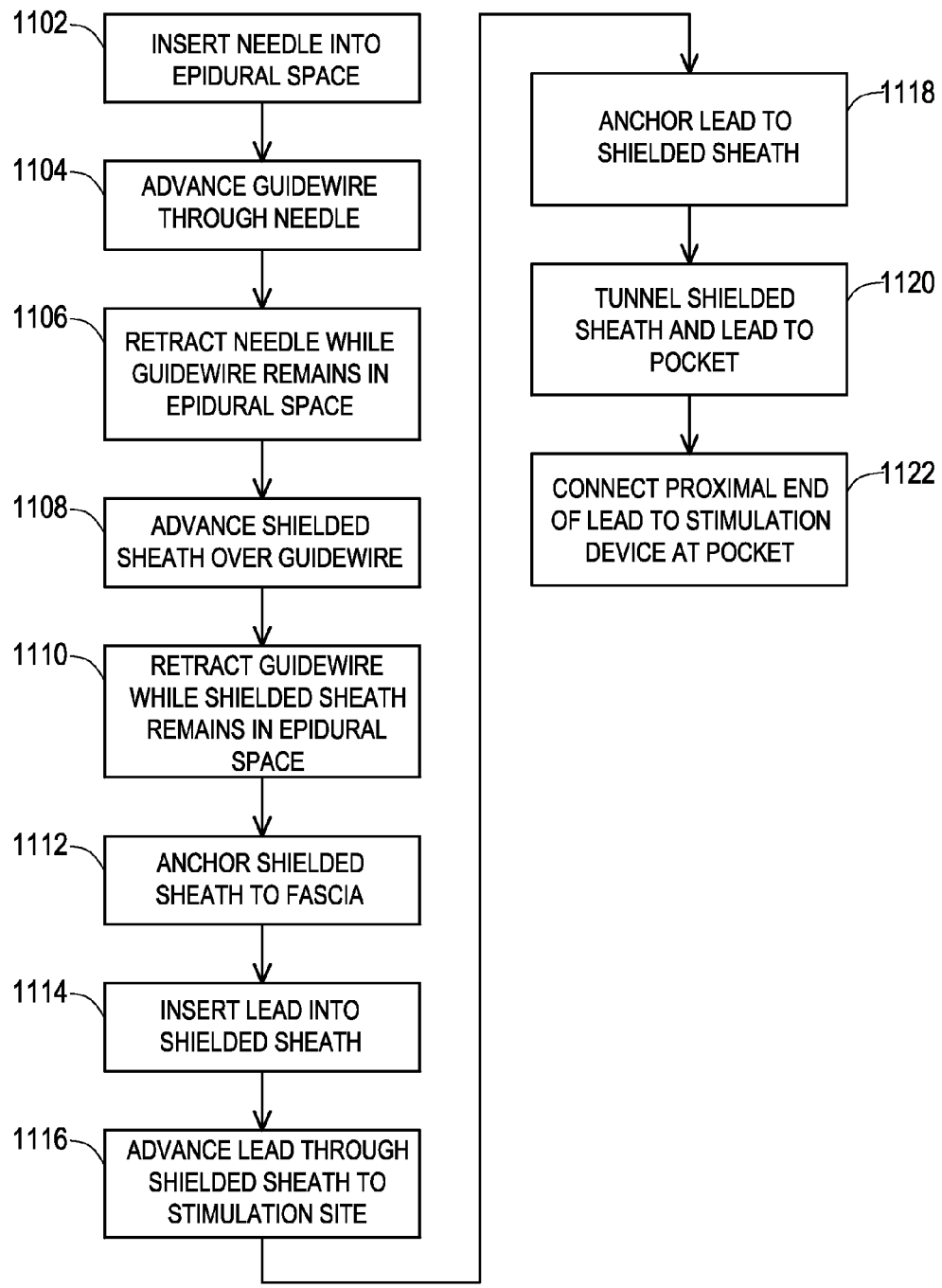
FIG. 11 shows a set of operations to implant a shielded sheath and an implantable medical lead according to the aspects shown in FIGS. 3-10.

In FIG. 11, the procedure for a new implantation of a lead 104 begins at an operation 1102 where a needle 304 as shown in FIG. 3 is being inserted through the spinal structures 308 and into the epidural space between the spinal structures 308 and the spinal cord 306. A guide wire 302 is then advanced through the needle 304 and into the epidural space at an operation 1104.

Figure 4:
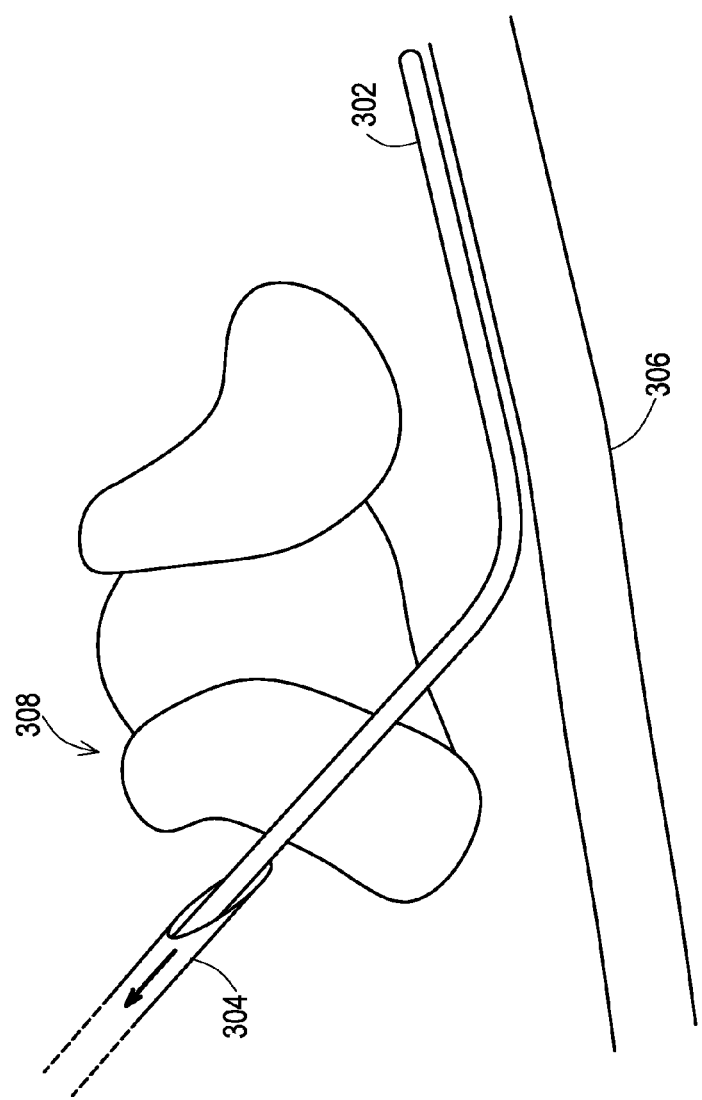
FIG. 4 shows the needle being removed from the epidural space while the guidewire remains.

At an operation 1106, the needle 304 is then retracted while the guidewire 302 remains in the epidural space. This is shown in FIG. 4 where it can be seen that the guidewire 302 has maintained a position within the epidural space as the needle 304 has exited the epidural space.

Figure 5:
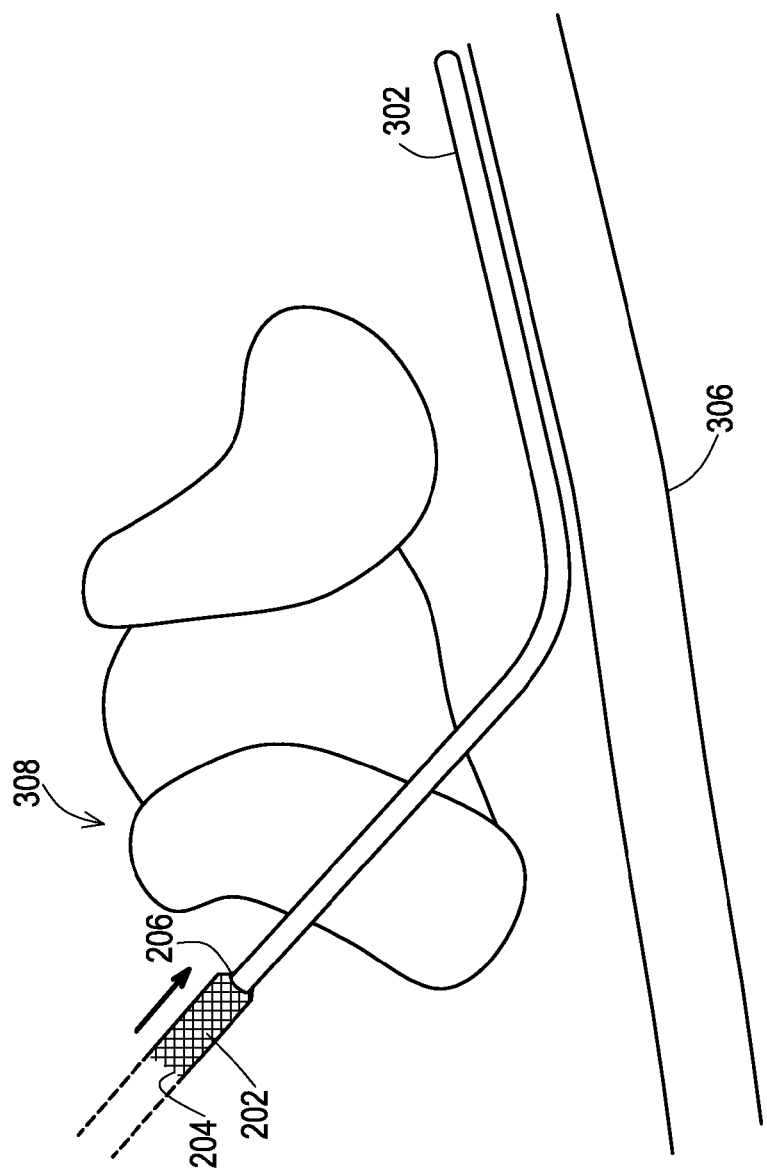
FIG. 5 shows an example of the shielded sheath being inserted into the epidural space by following along the guidewire.

At an operation 1108, the shielded sheath 202 having the shield layer 204 is advanced over the guidewire 302 and approaches the epidural space through the spinal structures 308. This is shown in FIG. 5. In this example, the shielded sheath 202 includes a tapered leading edge 206 which allows the shielded sheath 202 to more easily penetrate through the body tissues to reach the epidural space.

Figure 6:
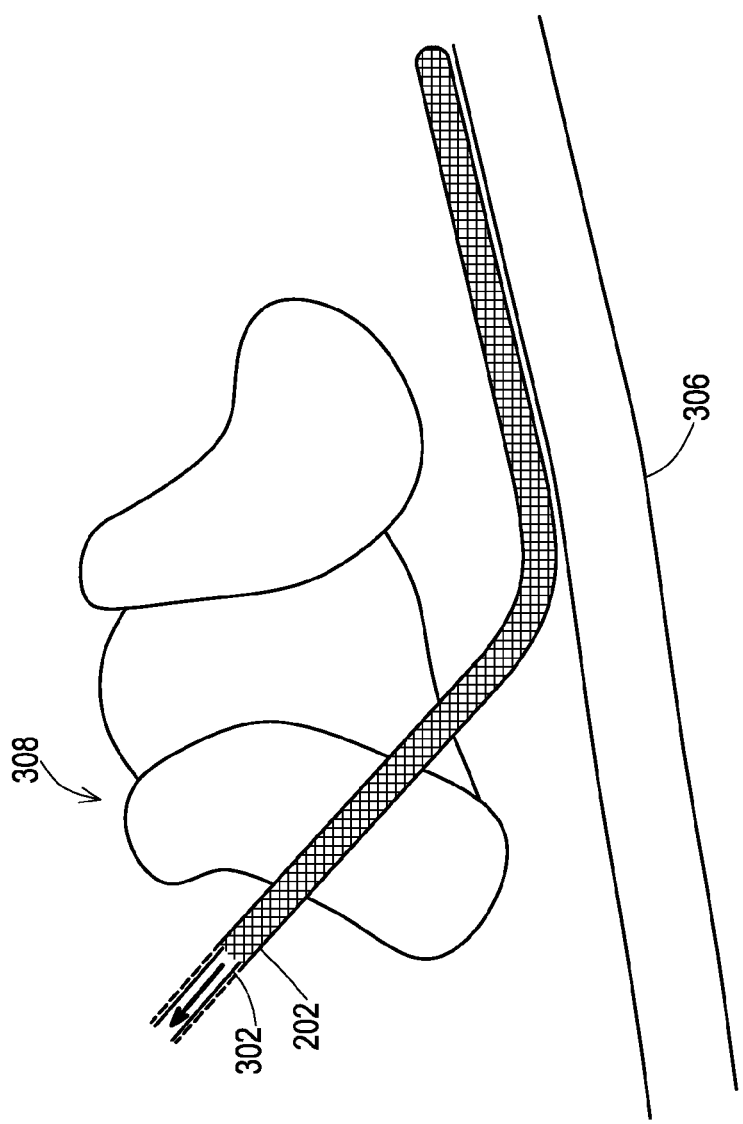
FIG. 6 shows removal of the guidewire from the epidural space while the shielded sheath remains.

At an operation 1110, the guidewire 302 is retracted from the epidural space through the shielded sheath 202 while the shielded sheath 202 remains in the epidural space. This is shown in FIG. 6 where it can be seen that the shielded sheath 202 has maintained a position within the epidural space as the guidewire 302 has exited the epidural space.

Figure 7:
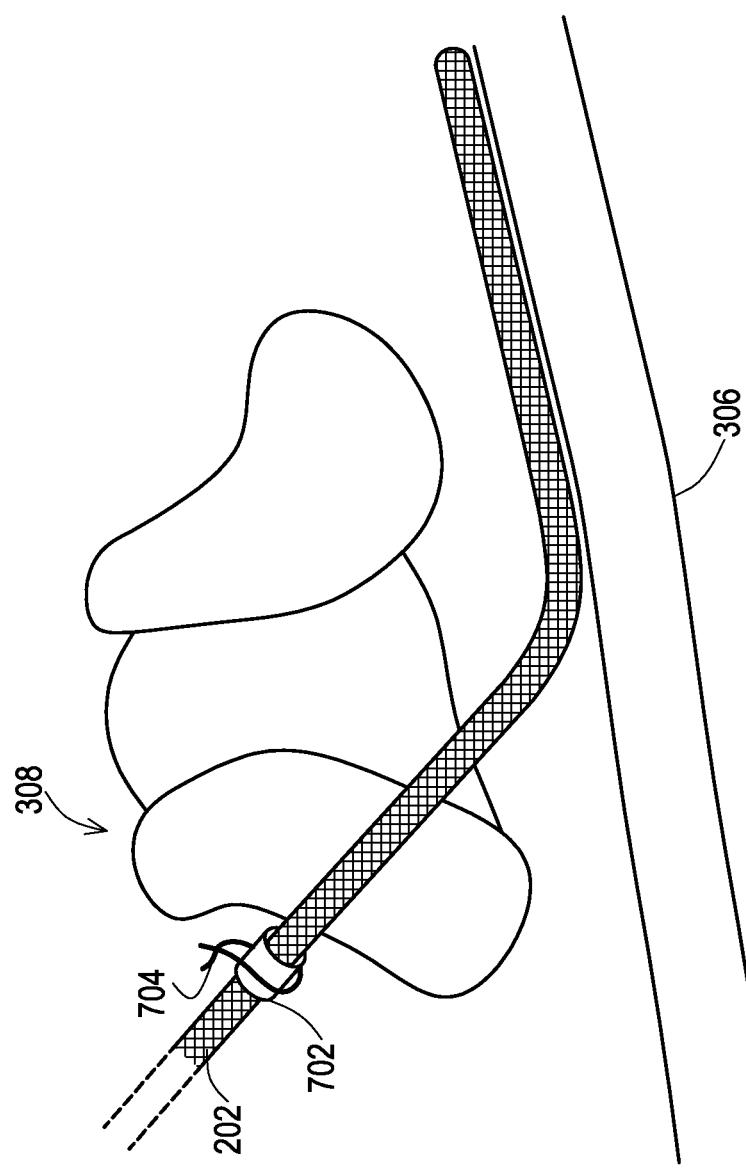
FIG. 7 shows an anchor being applied to hold the shielded sheath in place relative to the epidural space.

At an operation 1112, an anchor 702 as shown in FIG. 7 is applied to the shielded sheath 202 to fasten the shield to the surrounding fascia at the spinal structures 308. In the example shown in FIG. 7, the anchor 702 is of the type that forms a sleeve that is then affixed to surrounding tissue via sutures 704. However, other types of anchoring may also be used. For instance, the shielded sheath 202 may be directly sutured.

Figure 8:
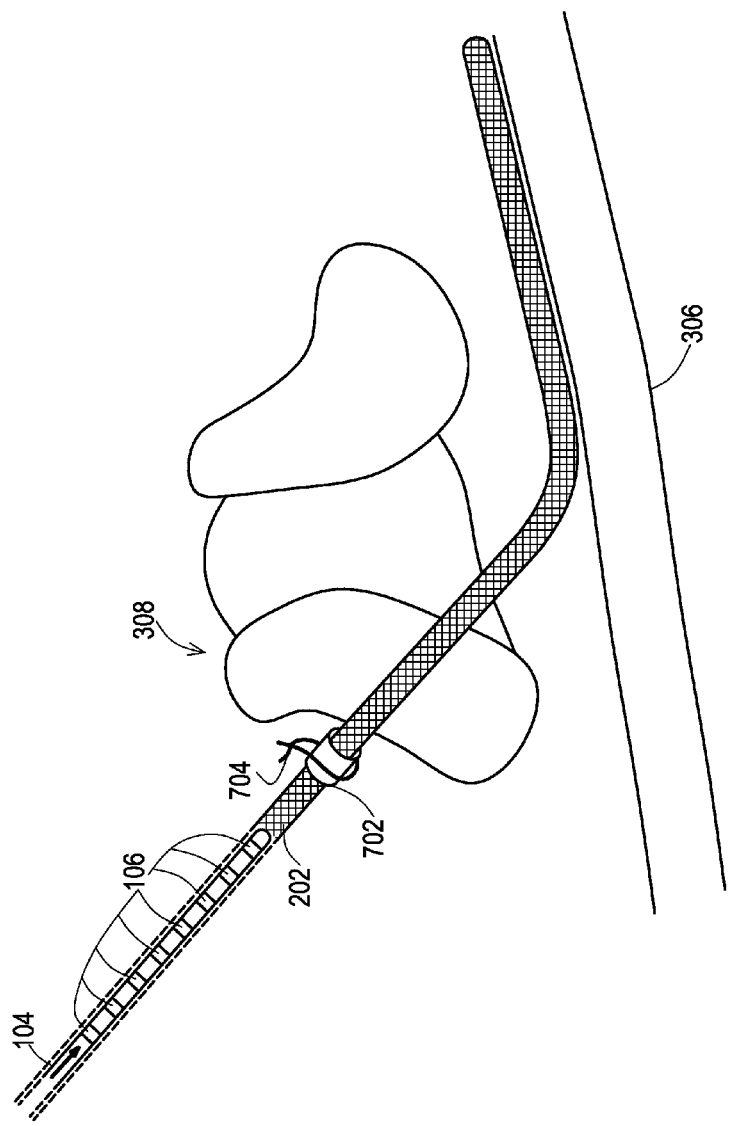
FIG. 8 shows an implantable medical lead being inserted into the epidural space by passing through the shield sheath.

At an operation 1114, the distal end of the lead 104 is inserted into the lumen of the shielded sheath 202 and is advanced toward the epidural space. This is shown in FIG. 8.

Figure 9:
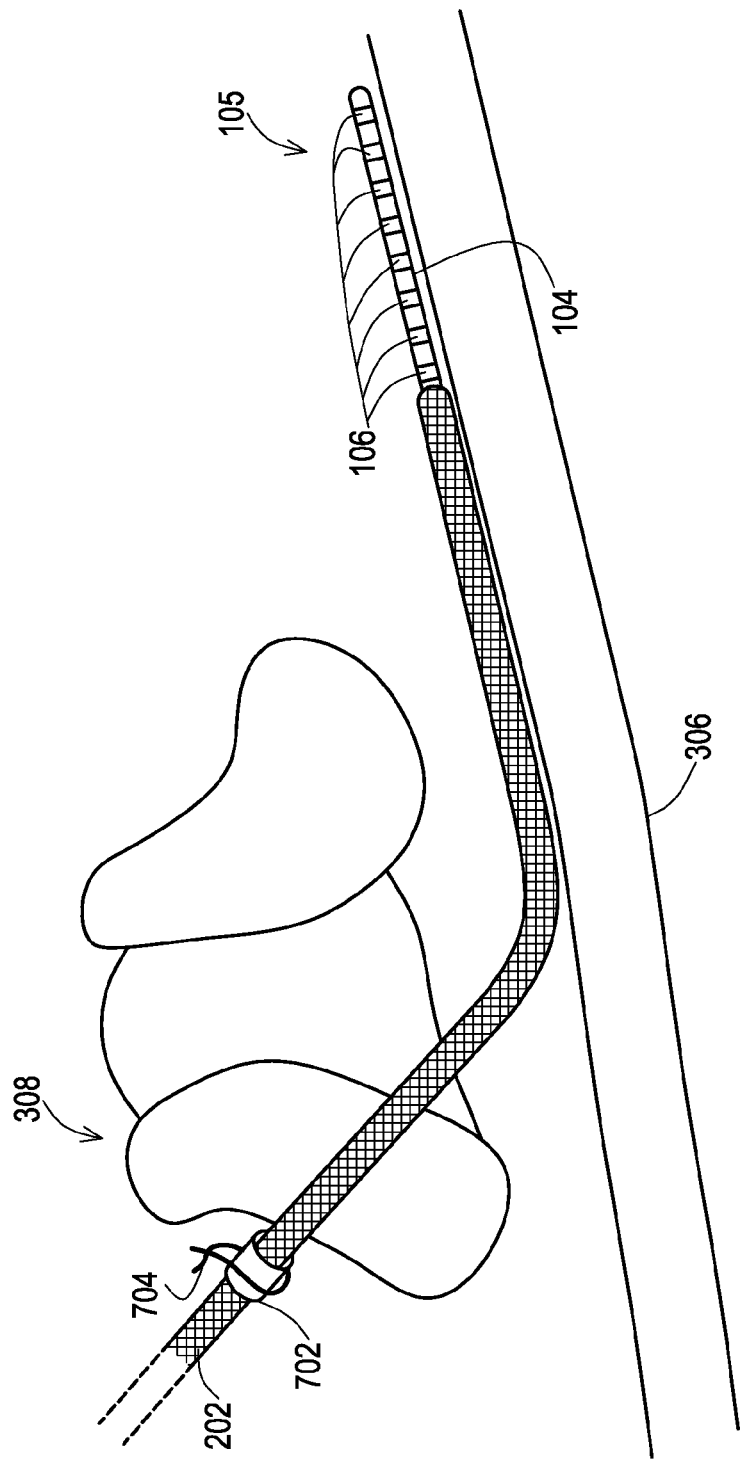
FIG. 9 shows distal end of the implantable medical lead exiting the distal end of the shielded sheath within the epidural space to reach the stimulation site.

At an operation 1116, the lead 104 is advanced through the shielded sheath 202 to the stimulation site. As shown in FIG. 9, the distal end 105 of the lead 104 exits from the shielded sheath to then reach the stimulation site within the epidural space with the electrodes 106 being exposed to the spinal cord 306.

Figure 10:
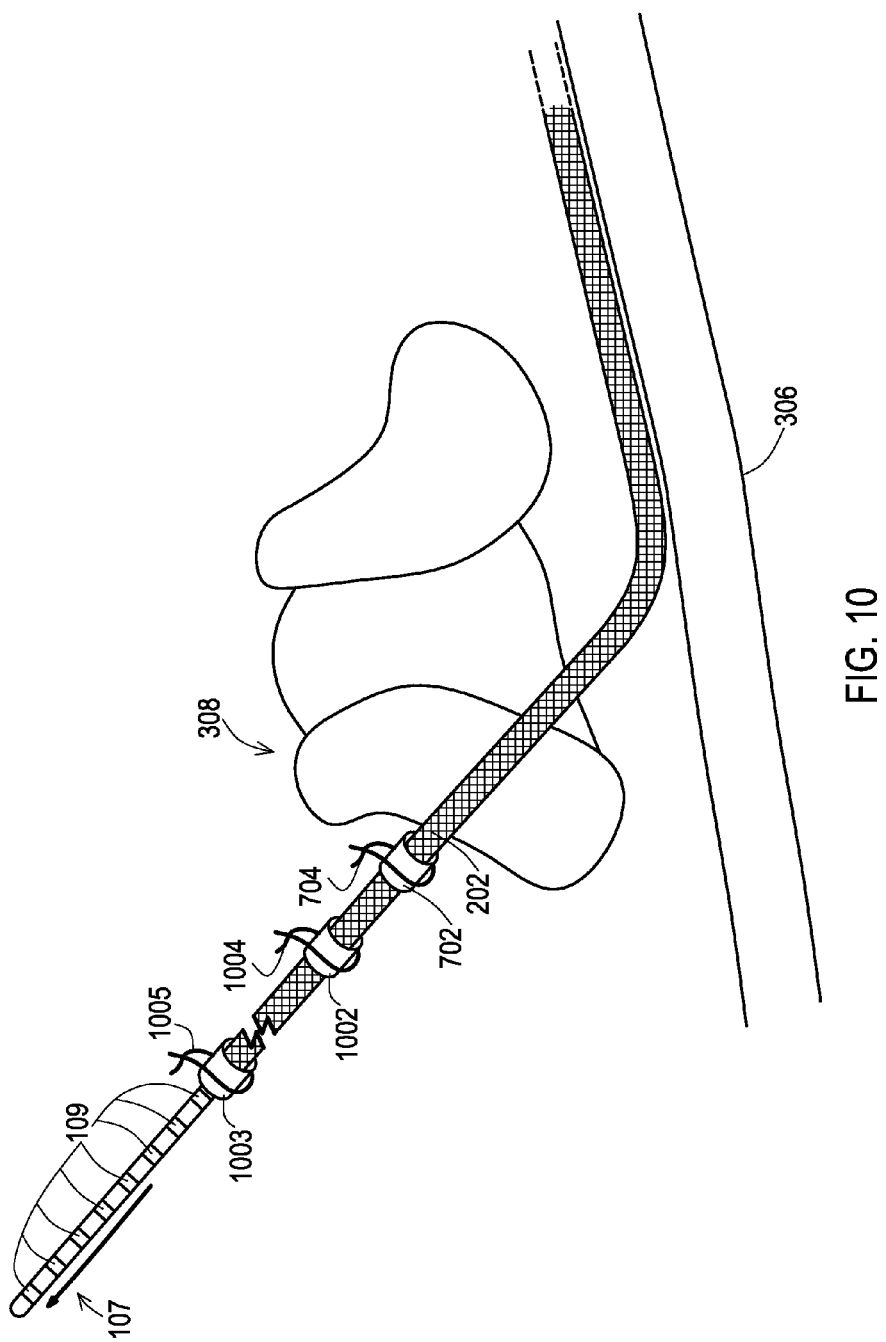
FIG. 10 shows an anchor being applied to hold the lead in place with the shielded sheath relative to the epidural space followed by the proximal end of the lead and shielded sheath being tunneled to the pocket for the implantable medical device.

At an operation 1118, an anchor 1002 as shown in FIG. 10 is applied to the shielded sheath 202 to further fasten the shield to the surrounding fascia at the spinal structures 308 while also anchoring the lead to the shielded sheath. This, in turn, anchors the lead to the surrounding fascia. In the example shown in FIG. 10, the anchor 1002 is also of the type that forms a sleeve that is then affixed to surrounding tissue via sutures 1004. In the example shown in FIG. 10, another anchor 1003 is also installed at the point where the lead 104 exits the proximal end of the shielded sheath and affixed to surrounding tissue via sutures 1005. By overlapping the point where the lead 104 exits the shielded sheath, this anchor 1003 is partially directly engaging the lead 104 and partially directly engaging the shielded sheath to further anchor the lead 104 and shielded sheath together and to the tissue. However, other types of anchoring may also be used for the purpose of anchoring the lead to the shielded sheath. For instance, the shielded sheath may be provided with elasticity of the insulative body and a slightly smaller lumen diameter than the lead 104 near the ends such that the compression of the shielded sheath may anchor the sheath to the lead 104. Other examples of anchoring include utilizing an anchor that is elastic and provides compression to force the sheath tightly against the lead.

At an operation 1120, the proximal end 107 of the lead 104 having proximal contacts 109 and the shielded sheath 202 are tunneled together to the pocket 114 where the implantable medical device 102 is or will be positioned. This is also shown in FIG. 10.

At an operation 1122, the proximal end 107 of the lead 104 is connected to the implantable medical device 102 at the pocket 114. The proximal contacts 109 of the lead 104 establish electrical connections with corresponding electrical connectors of the implantable medical device 102 to complete the stimulation pathway to the electrodes 106 that are positioned at the stimulation site within the epidural space.

Figure 17:
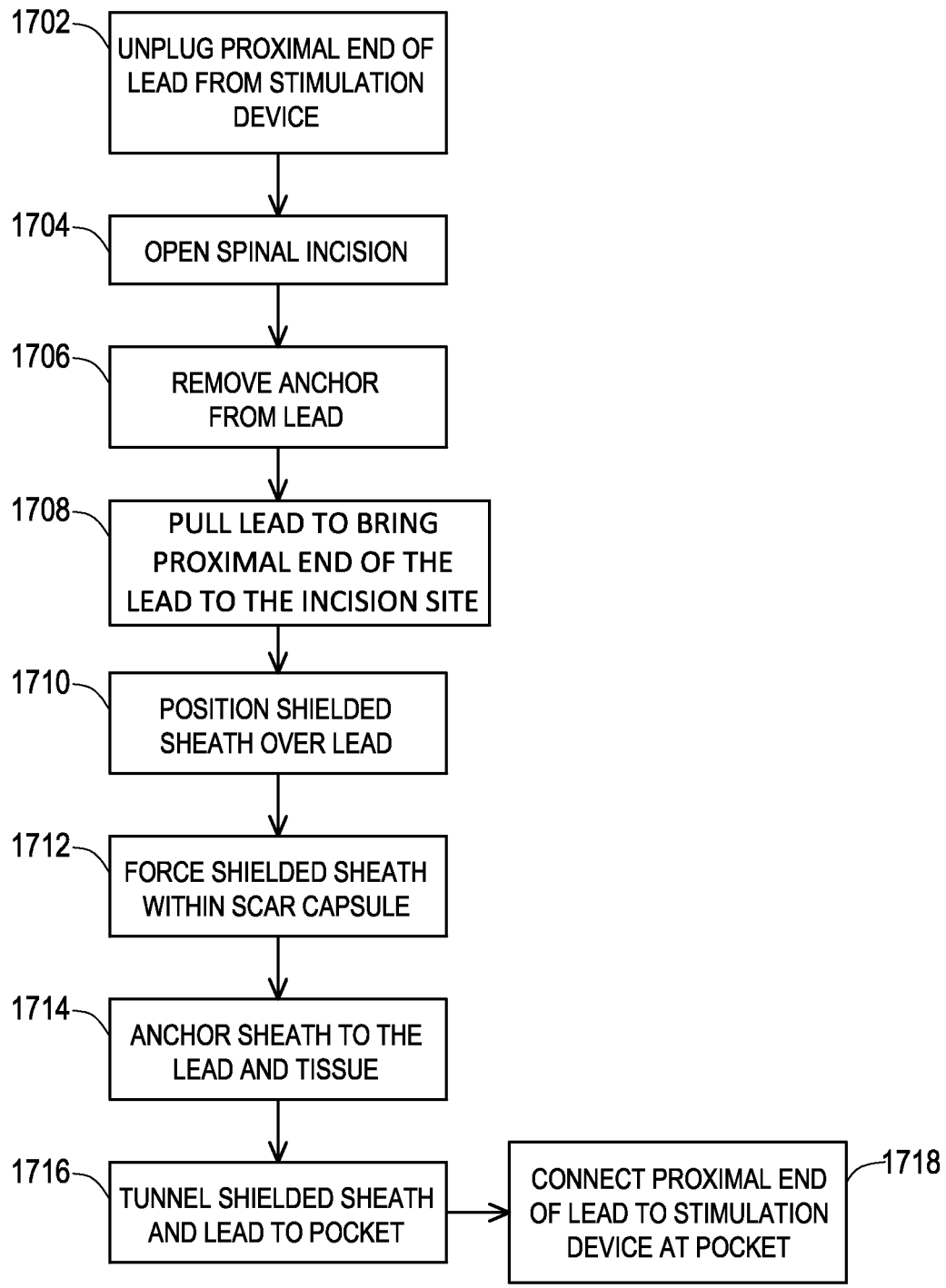
FIG. 17 shows a set of operations to add a shielded sheath over an implanted lead according to the aspects shown in FIGS. 12-16.

In FIG. 17, the procedure for a previously implanted lead 104 begins at an operation 1702 where the proximal end of the lead 107 is unplugged from the implantable medical device 102. A spinal incision is then opened nearby the entry site to the epidural space at an operation 1704.

Figure 12:
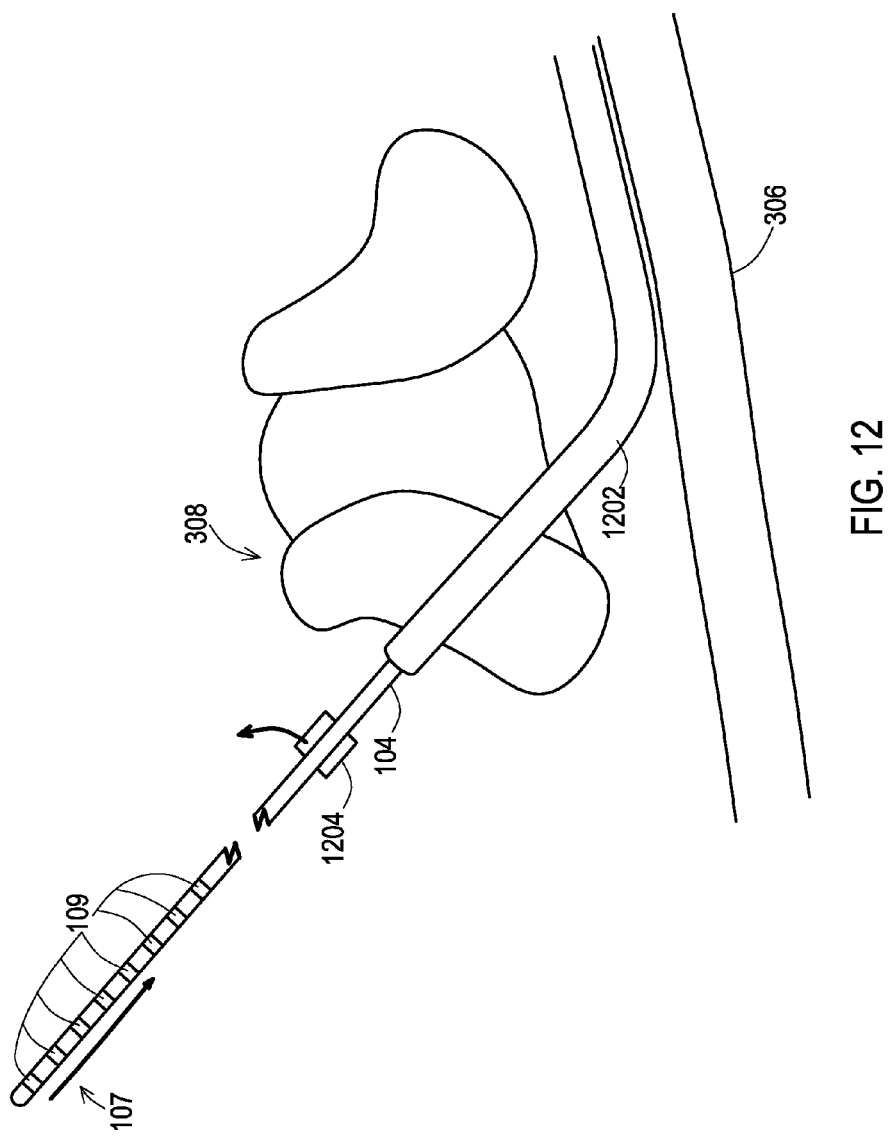
FIG. 12 shows an example of a procedure that begins with an anchor being removed from a lead that is implanted with a distal end in the epidural space and a proximal end of the lead being pulled to the incision site for entry to the epidural space.

At an operation 1706, an anchor 1204 as shown in FIG. 12 is being removed from the lead 104. Then, at an operation 1708, the lead 104 is pulled at the incision site to bring the proximal end 107 of the lead 104 to the incision cite. This is also shown in FIG. 12. It can further be seen in FIG. 12 that the distal end of the lead 104 is present within a scar capsule 1202 that has naturally formed about the distal end of the lead 104.

Figure 13:
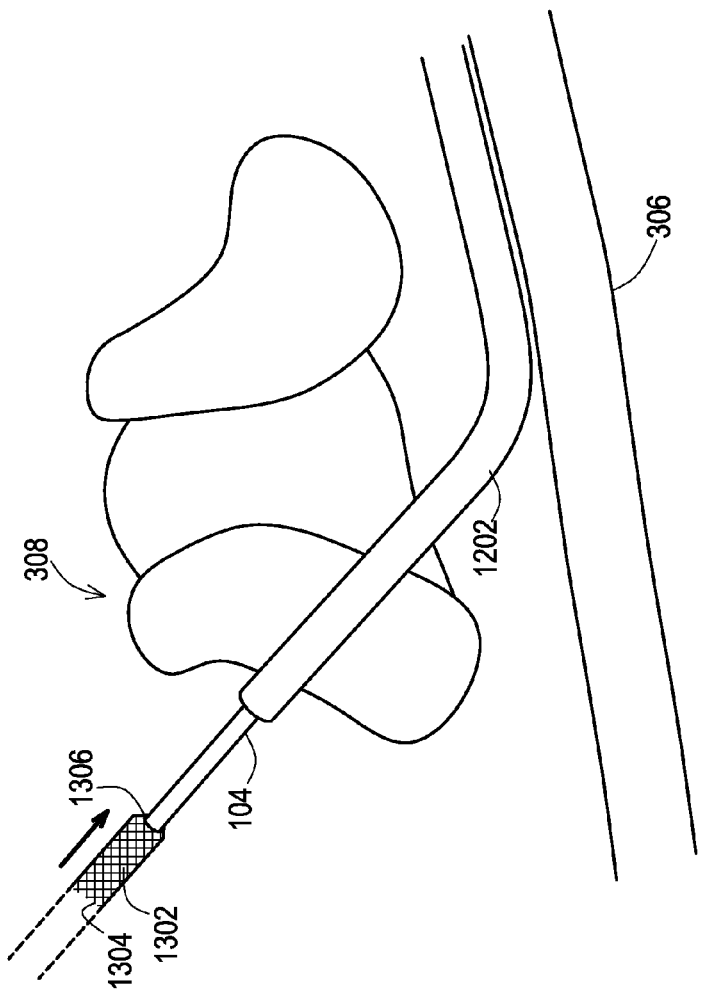
FIG. 13 shows an example of the shielded sheath being inserted over the implanted lead.

At an operation 1710, a shielded sheath 1302 is positioned over the lead 104 with the proximal end 107 of the lead 104 entering the lumen of the shielded sheath 202. This is shown in FIG. 13. The shielded sheath 1302 may be the same or different construction as the shielded sheath 202 and includes a shield layer 1304 that may be the same or different construction as the shield layer 204.

Figure 14:
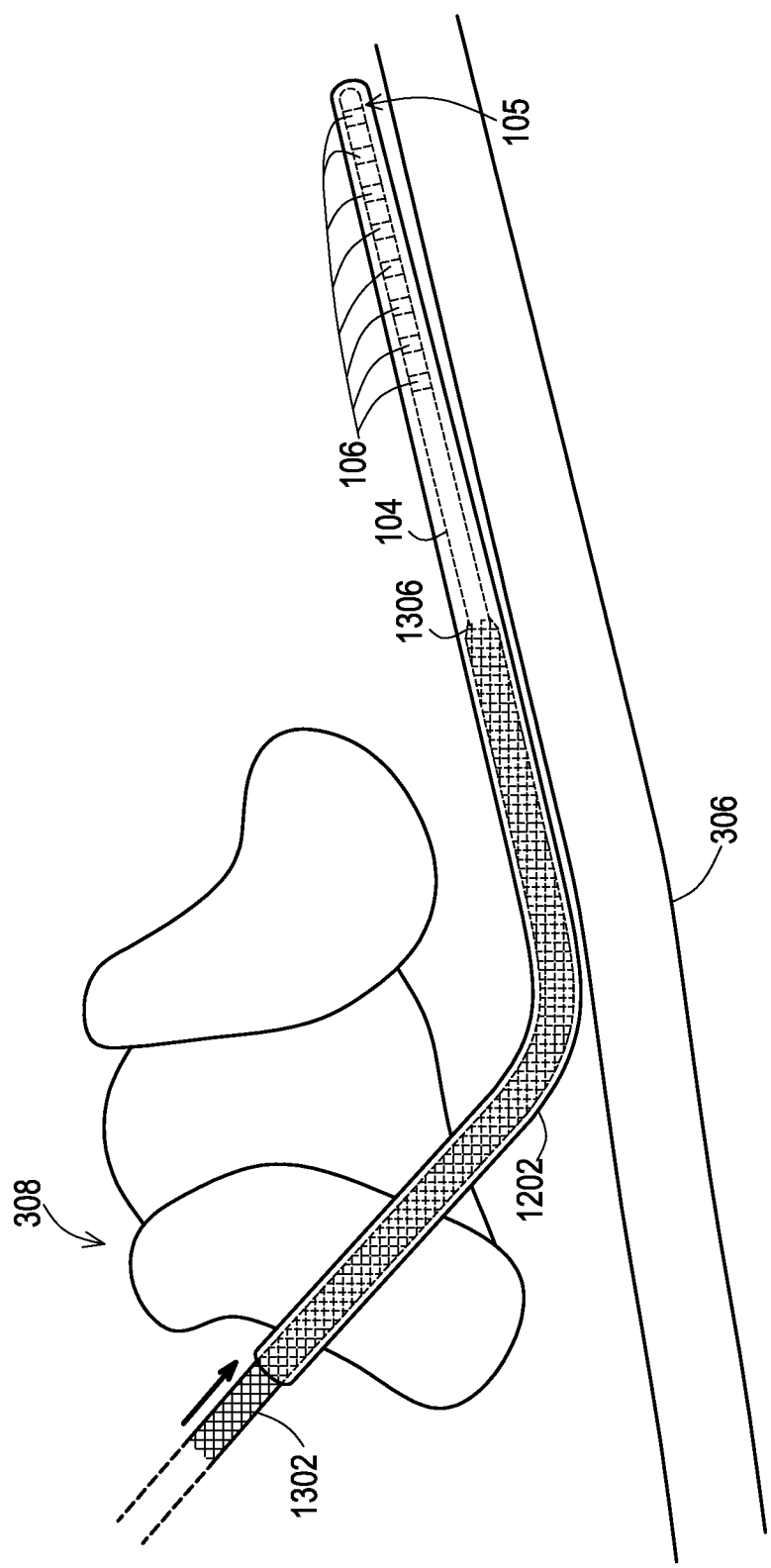
FIG. 14 shows the shield sheath passing through a scar capsule that surrounds the implanted lead and passing into the epidural space.

At an operation 1712, the shielded sheath 1302 is forced within the scar capsule 1202. A tapered leading edge 1306 may be included on the shielded sheath 1302 to assist in penetrating into the scar capsule 1202. This is shown in FIG. 14. The shielded sheath is advanced through the scar capsule until reaching a desired position proximal of the electrodes 106 on the distal end 105 of the lead 104 as shown in FIG. 15.

Figure 15:
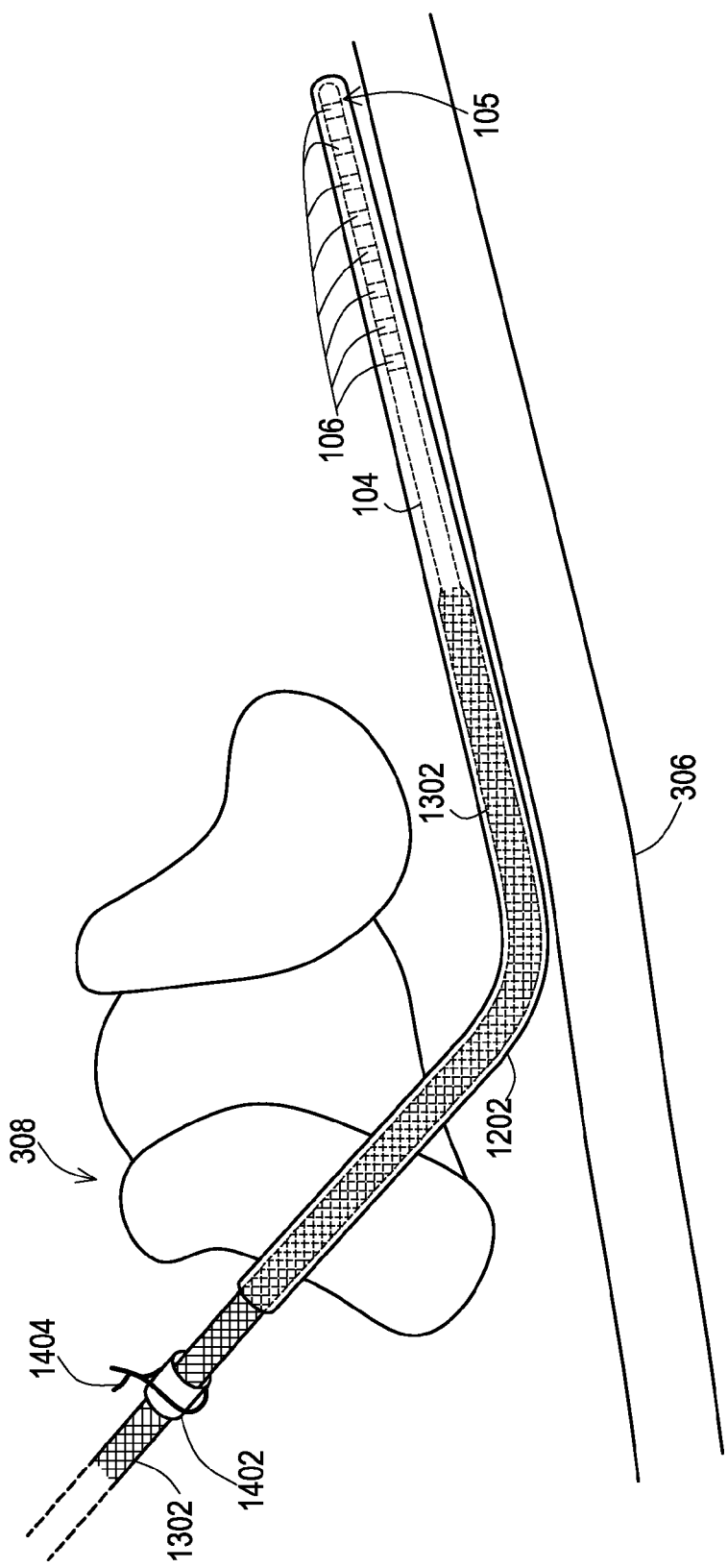
FIG. 15 shows an anchor being applied to hold the shielded sheath and lead in place relative to the epidural space.

At an operation 1714, an anchor 1402 as also shown in FIG. 15 is applied to the shielded sheath 1302 to fasten the shielded sheath 1302 to the surrounding fascia at the spinal structures 308 while also anchoring the lead 104 to the shielded sheath 1302. This, in turn, anchors the lead 104 to the surrounding fascia. In the example shown in FIG. 15, the anchor 1402 is also of the type that forms a sleeve that is then affixed to surrounding tissue via sutures 1404. However, other types of anchoring may also be used for the purpose of anchoring the lead to the shielded sheath. For instance, the shielded sheath may be provided with elasticity of the insulative body and a slightly smaller lumen diameter than the lead 104 near the ends such that the compression of the shielded sheath may anchor the sheath to the lead 104. Other examples of anchoring include utilizing an anchor that is elastic and provides compression to force the sheath tightly against the lead.

Figure 16:
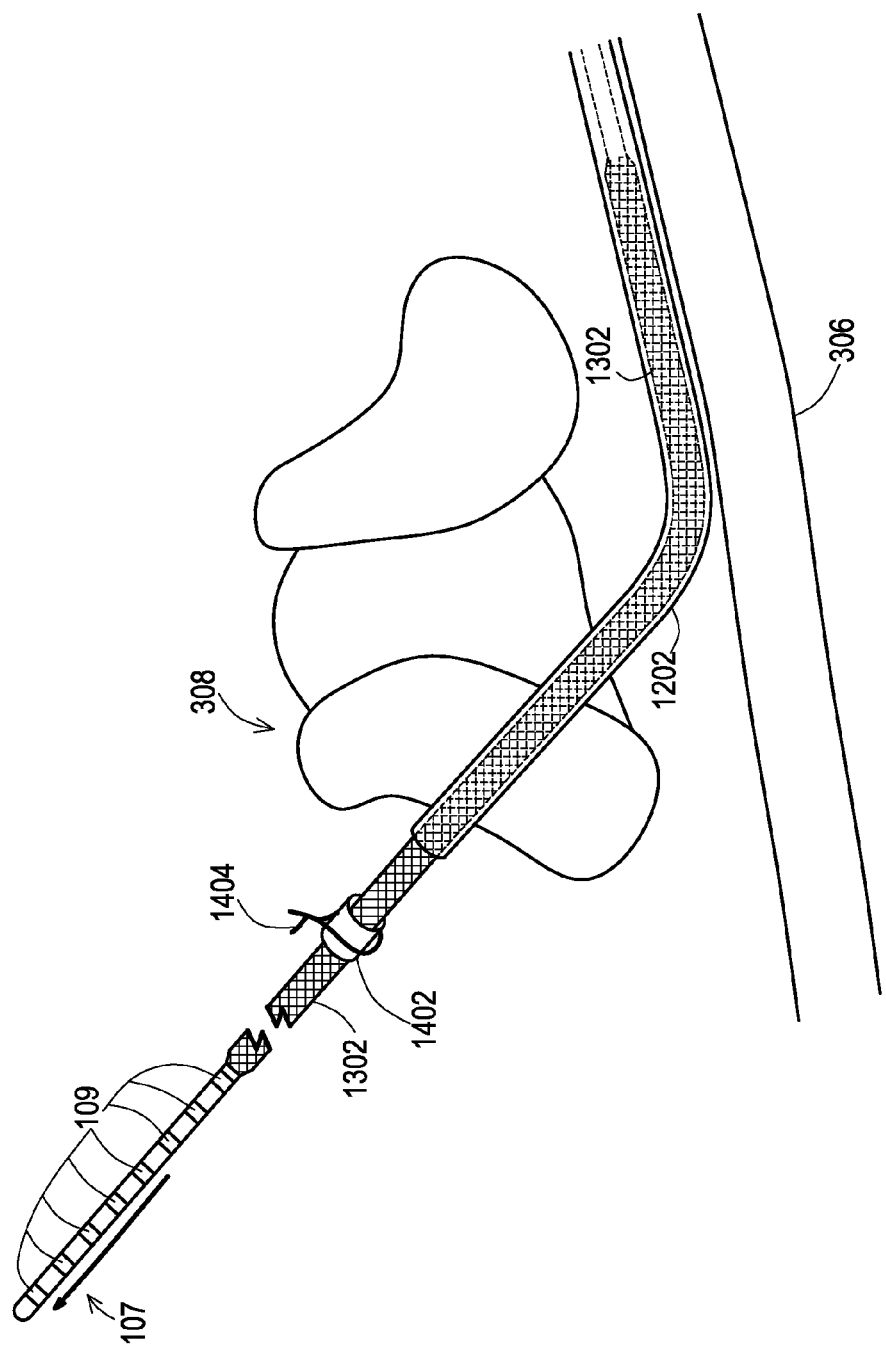
FIG. 16 shows the proximal end of the lead and shielded sheath being tunneled to the pocket for the implantable medical device.

At an operation 1716, the proximal end 107 of the lead 104 having proximal contacts 109 and the shielded sheath 1302 are tunneled together to the pocket 114 where the implantable medical device 102 is or will be positioned. This is shown in FIG. 16.

At an operation 1718, the proximal end 107 of the lead 104 is connected to the implantable medical device 102 at the pocket 114. The proximal contacts 109 of the lead 104 establish electrical connections with corresponding electrical connectors of the implantable medical device 102 to complete the stimulation pathway to the electrodes 106 that are positioned at the stimulation site within the epidural space.

Figure 18:
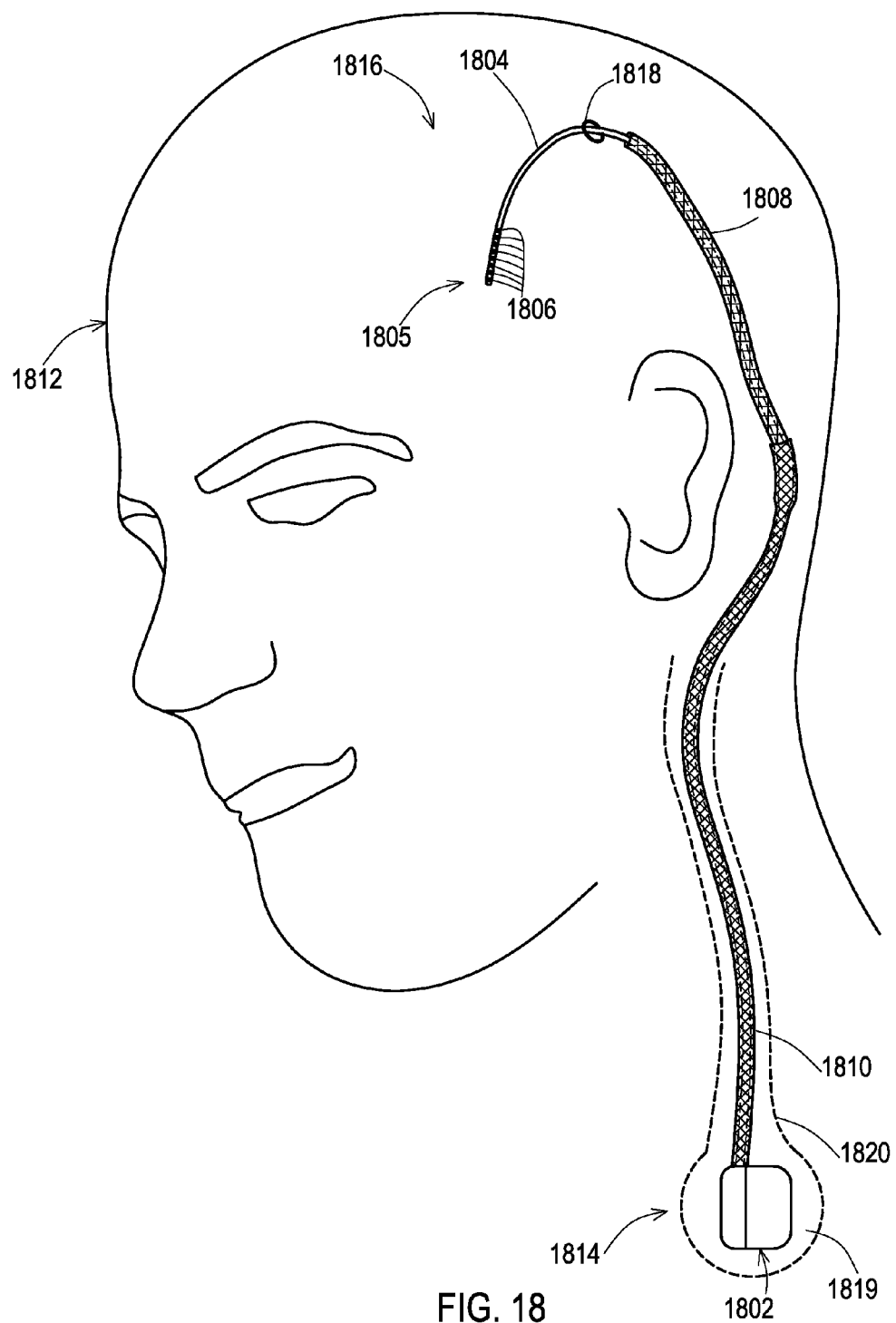
FIG. 18 shows another example of an implantable medical system including a lead extension with shielded sheaths installed over a lead and a lead extension.

FIG. 18 shows an implantable medical system 1814 which includes an implantable medical device 1802, an implantable medical lead 1804, and a lead extension that is connected between the lead 1804 and the implantable medical device 1802. The implantable medical device 1802 is positioned within a pocket 1819 formed in the upper torso and the lead extension extends through a subcutaneous tunnel 1820 formed when implanting the extension. The proximal end 1805 of the lead 1804 passes through the cranium via a hole 1818 to reach a stimulation site within the brain 1816 of the patient 1812.

The system 1814 also includes a first shielded sheath 1808 that has been placed over the lead 1804 and a second shielded sheath 1810 that has been placed over the lead extension. The shielded sheath 1808 is positioned between the proximal end where the lead 1804 connects to the extension and the distal end 1805 where the electrodes 1806 are located. The shielded sheath 1810 is positioned between the proximal end where the extension connects to the implantable medical device and the distal end where a connector housing is located. The shielded sheaths may be constructed like the examples discussed above for shielded sheath 202 and 2600. A cranial anchor may be installed onto the lead 1804 at the hole 1818 and the sheath 1808 naturally maintains its position between the hole 1818 and the distal connector 2102 of the extension 2104. Likewise, the second sheath 1810 naturally maintains its position between the distal end of the distal connector 2102 and the proximal end of the extension 2104. However, if desired, anchoring may be provided on the sheath 1808 and second sheath 1810 in this instance as well in the same manners as discussed above with respect to the spinal implantations.

Figure 19:
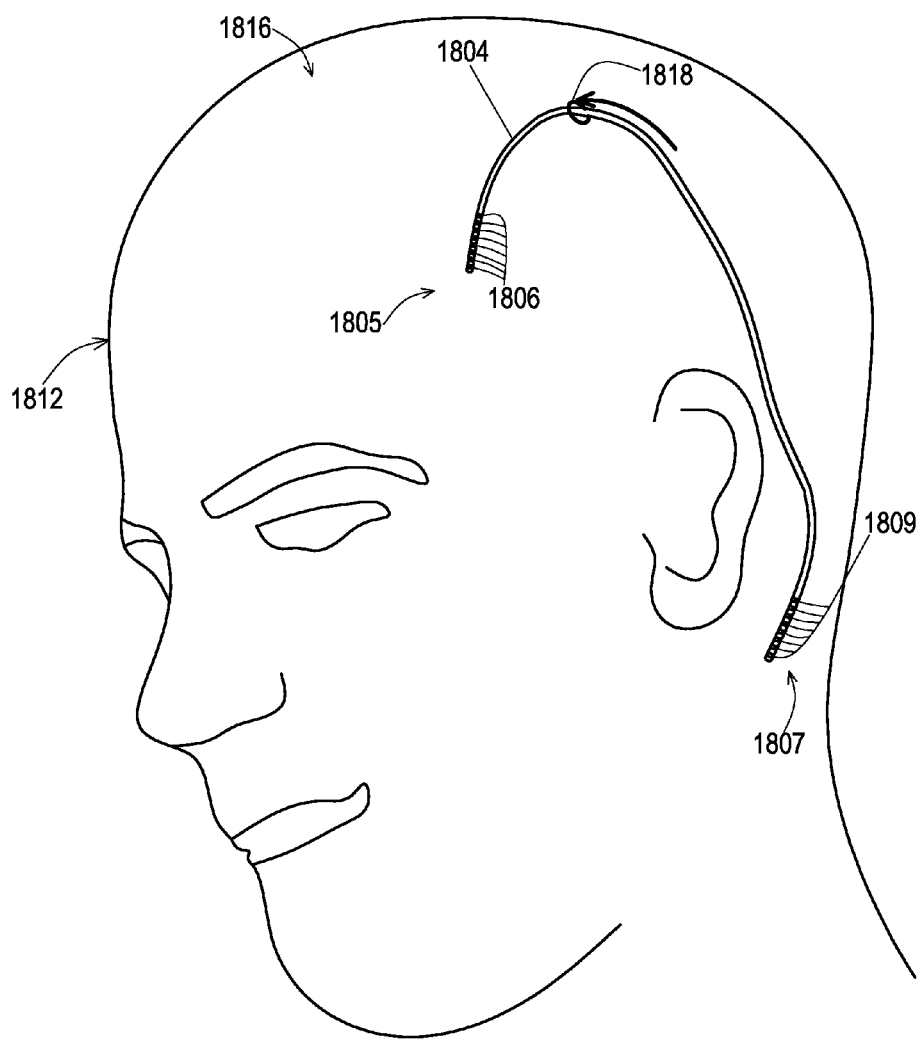
FIG. 19 shows an example of a procedure that begins with a lead being tunneled to a bore hole with a distal end of the lead being inserted into the brain to a stimulation site.
Figure 23:
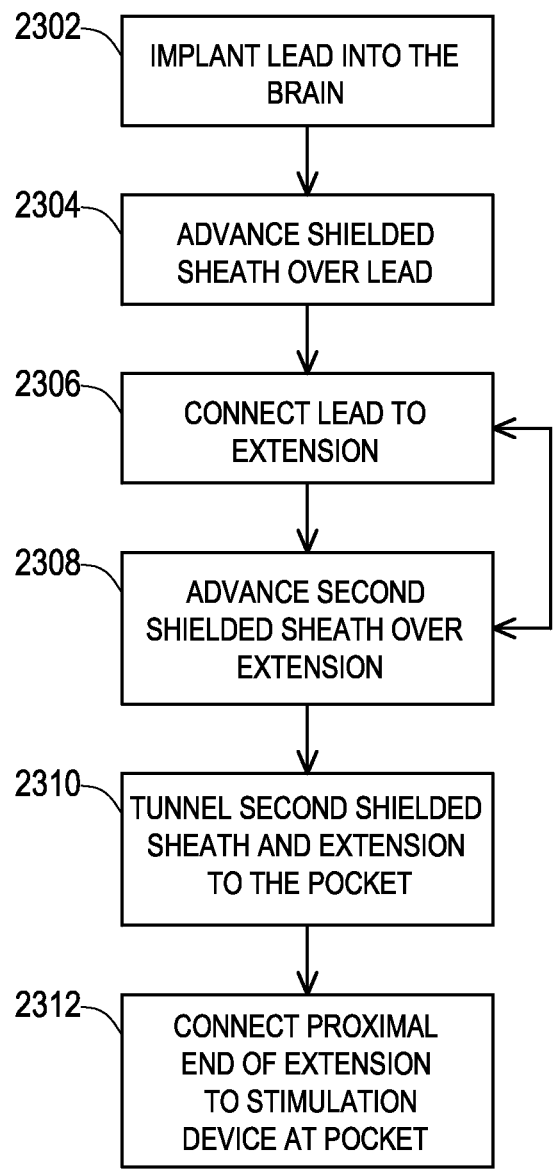
FIG. 23 shows a set of operations to add a shielded sheath over the implanted lead and to add a second shielded sheath over the implanted extension according to the aspects shown in FIGS. 19-22.

In FIG. 23, the procedure for implanting the lead 1804, extension, and shielded sheaths 1808, 1810 begins at an operation 2302 where the lead 1804 as shown in FIG. 19 is being inserted through the hole 1818 of the cranium and into the brain 1816. The lead 1804 may be routed subcutaneously from an area behind the ear of the patient up to the hole 1818. The lead 104 may be anchored nearby the hole 1818.

Figure 20:
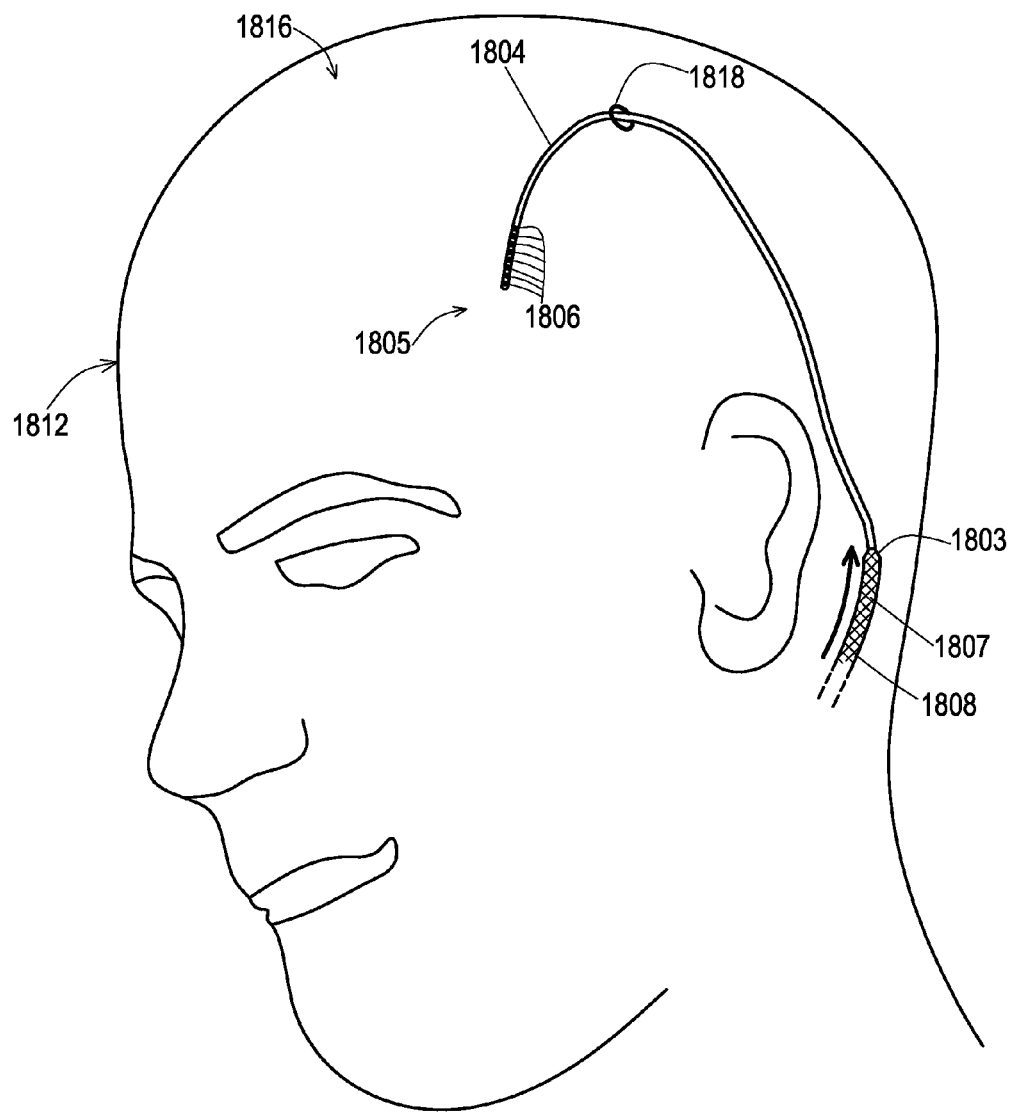
FIG. 20 shows an example of a shielded sheath being inserted over the lead.

In an operation 2304, the first shielded sheath 1808 is advanced over the lead 104. The proximal end of the lead 104 is inserted into the lumen of the shielded sheath 1808 and the shielded sheath 1808 is advanced toward the hole 1818. This is shown in FIG. 20. It can be seen that the shielded sheath 1808 has a tapered leading edge 1803 that assists in passing subcutaneously toward the hole 1818. It can also be seen that the shielded sheath 1808 has a shield layer 1807.

Figure 21:
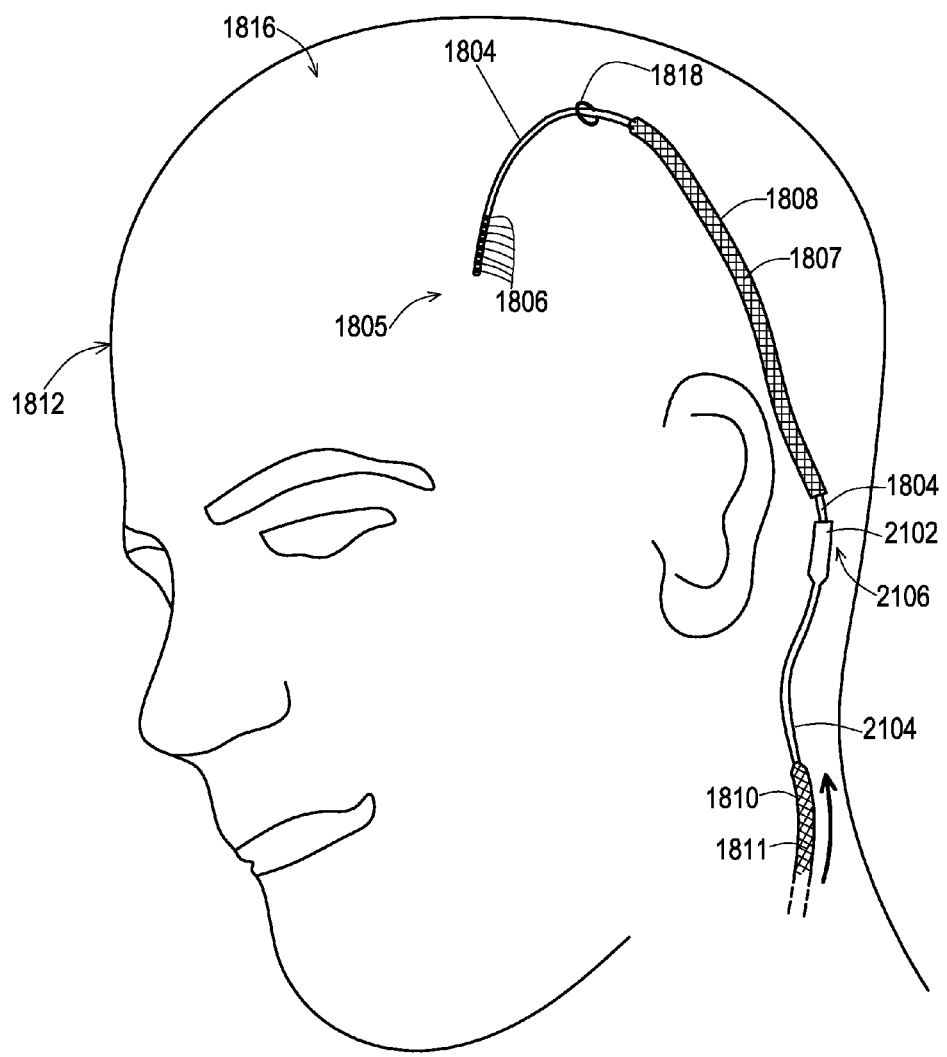
FIG. 21 shows an example of a second shielded sheath being inserted over a lead extension that has been tunneled and connected to a proximal end of the lead.

In an operation 2306, the proximal end of the lead 1804 is connected to the distal end connector 2102 on a distal end 2106 of the lead extension 2104 as shown in FIG. 21. This occurs via an incision site that has been created when initially tunneling the lead to the hole 1818. As also shown in FIG. 21, the second shielded sheath 1810 having a shield layer 1811 is advanced over the lead extension 2104 at an operation 2308.

Figure 22:
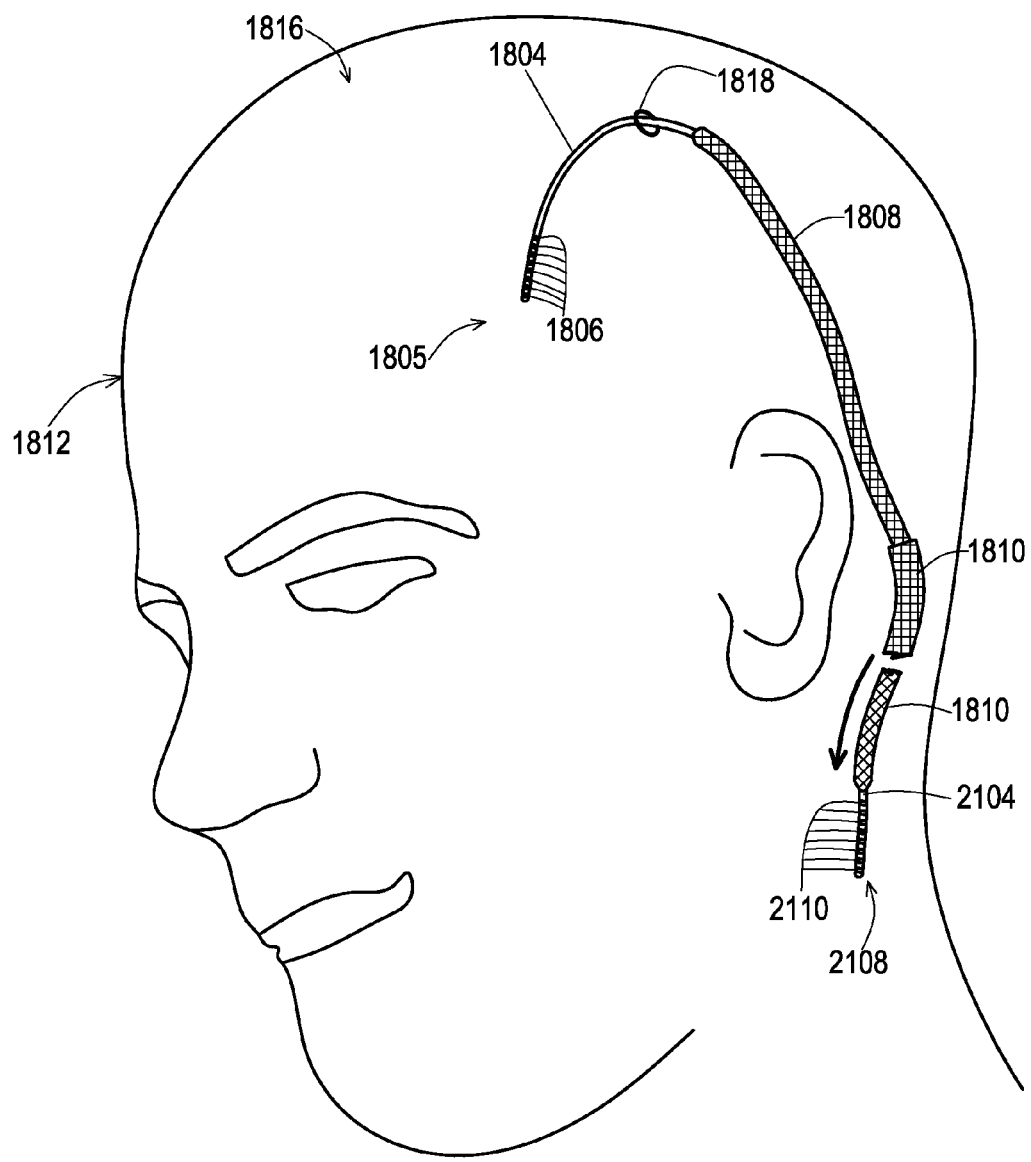
FIG. 22 shows the proximal end of the extension and the second shielded sheath being tunneled to the pocket for the implantable medical device.

In an operation 2308, the proximal end 2108 of the extension 2104 having proximal contacts 2110 and the second shielded sheath 1810 are tunneled together to the pocket 1819 where the implantable medical device 1802 is or will be positioned. This is shown in FIG. 22.

At an operation 2312, the proximal end 2108 of the extension 2104 is connected to the implantable medical device 1802 at the pocket 1819. The proximal contacts 2110 of the extension 2104 establish electrical connections with corresponding electrical connectors of the implantable medical device 1802 to complete the stimulation pathway to the electrodes 1806 that are positioned at the stimulation site within the brain 1816.

Figure 24:
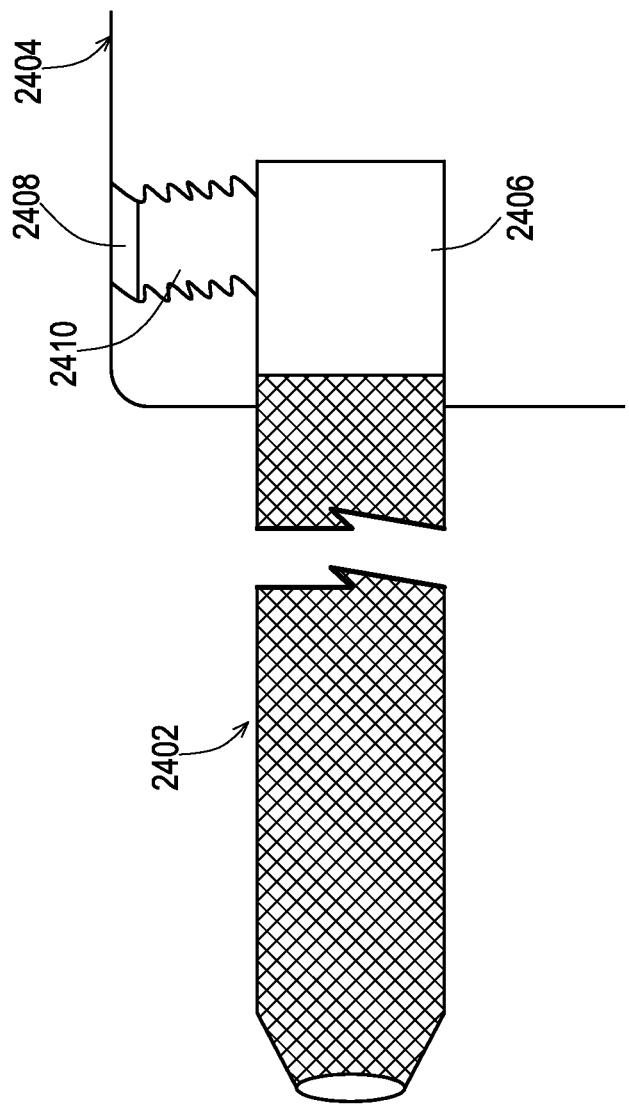
FIG. 24 shows a proximal end of an example of a shielded sheath that may include a connector for engagement with a contact of an implantable medical device.

FIG. 24 shows an example of a shielded sheath 2402 that may be placed over a lead or an extension where the proximal end of the shielded sheath 2402 provides connectivity. In this example, a proximal contact 2406 such as a metal ring is positioned on the proximal end. This proximal contact 2406 may be in physical contact with the shield layer of the shielded sheath 2402 to provide an electrical connection from the shield layer to the proximal contact 2406. An implantable medical device 2404 may receive the proximal end of the shielded sheath 2402 into a bore where the lead or lead extension may also be inserted.

The implantable medical device 2404 may include an electrical connector such as a set screw 2410 and a corresponding set screw bore 2408 that allows a physical connection to be made with the proximal contact. This electrical connector 2410 then provides an electrical pathway to a grounding surface at the implantable medical device such as a metal housing. This effectively provides a tissue ground at the implantable medical device 2404 for the shield layer of the shielded sheath 2402 such that RF energy coupled to the shield may be diverted to the grounding surface and surrounding tissue of the implantable medical device 2404.

Figure 25:
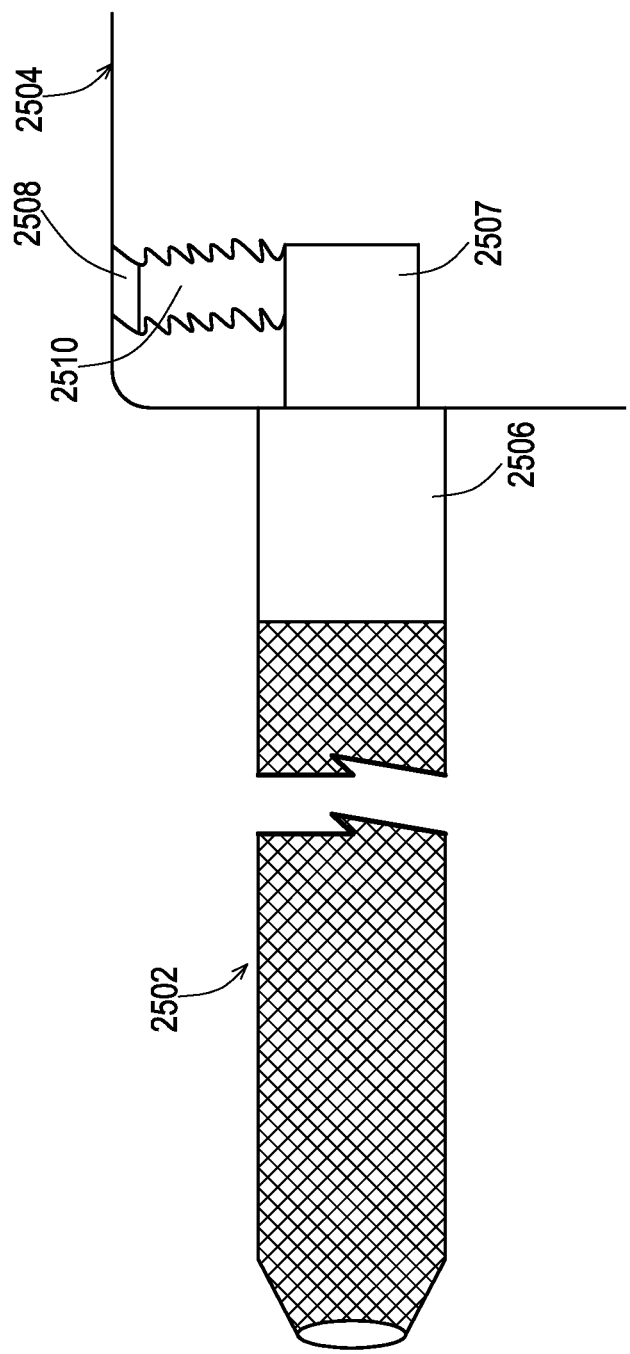
FIG. 25 shows a proximal end of another example of a shielded sheath that may include a connector with a reduced diameter portion for engagement with a contact of an implantable medical device.

FIG. 25 shows an example of a shielded sheath 2502 that may be placed over a lead or an extension where the proximal end of the shielded sheath 2502 also provides connectivity. In this example, a proximal contact 2506 such as a metal ring is positioned on the proximal end. This proximal contact 2506 may be in physical contact with the shield layer of the shielded sheath 2502 to provide an electrical connection from the shield layer to the proximal contact 2506. The proximal contact 2506 also includes a smaller diameter region 2507. An implantable medical device 2404 may receive the proximal end of the shielded sheath 2402 and specifically the smaller diameter region 2507 of the proximal contact 2506 into a bore where the lead or lead extension may also be inserted. This bore may have a diameter that is smaller than the larger diameter region of the proximal contact 2506 but large enough to accept the smaller diameter region 2507.

The implantable medical device 2504 may include an electrical connector such as a set screw 2510 and a corresponding set screw bore 2508 that allows a physical connection to be made with the proximal contact region 2507. This electrical connector 2510 then provides an electrical pathway to a grounding surface at the implantable medical device such as a metal housing. This example also effectively provides a tissue ground at the implantable medical device 2504 for the shield layer of the shielded sheath 2502 such that RF energy coupled to the shield may be diverted to the grounding surface and surrounding tissue of the implantable medical device 2504.

Figure 27:
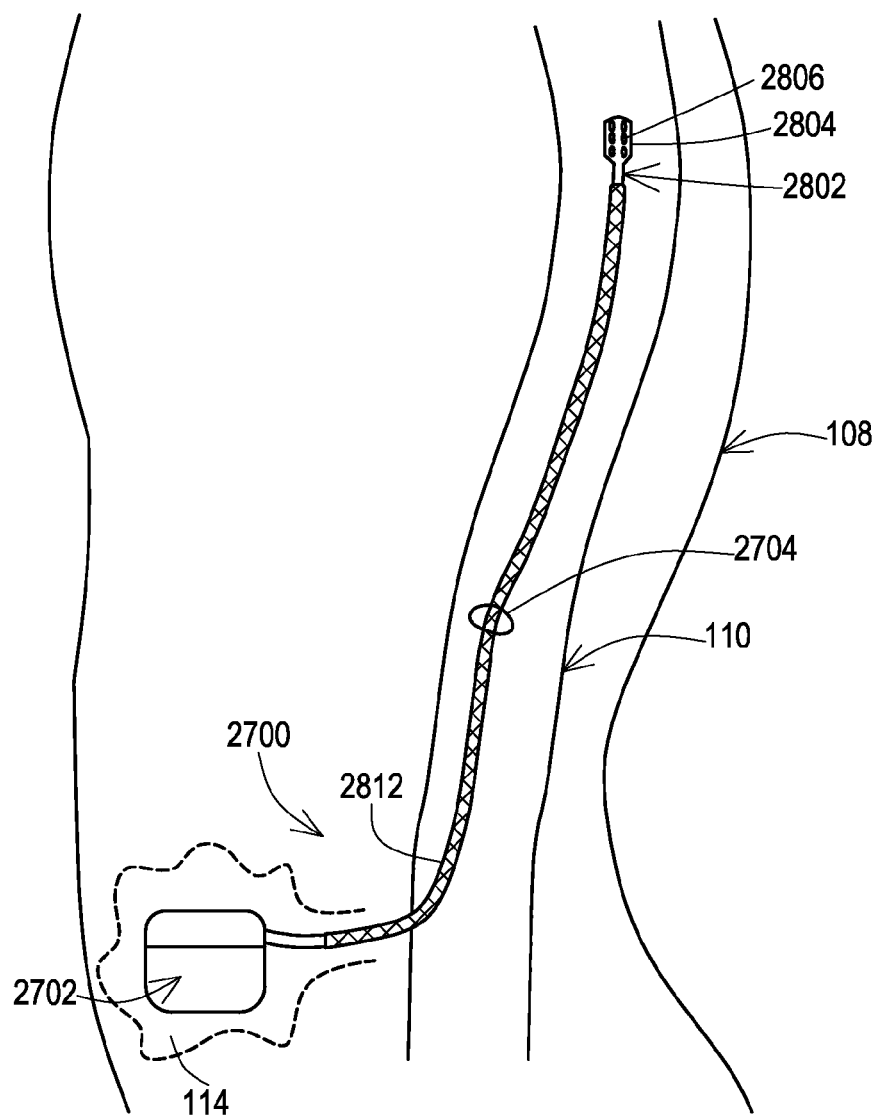
FIG. 27 shows an implantable medical system with the shielded sheath installed over a paddle lead.

FIG. 27 shows an implantable medical system 2700 that is implanted into the patient 108 and is similar to the implantable medical system of FIG. 2 except that the implantable medical system 2700 includes an implantable medical paddle lead 2802. The paddle lead 2802 has been implanted via an entry point 2704, typically created through a surgical procedure to create adequate space for the paddle portion 2806, and extends into the epidural space of the spine 110. The paddle lead 2802 includes a paddle portion 2804 that includes an array of electrodes 2806. The paddle lead 2802 is connected to an implantable medical stimulation device 2702 that is located in a pocket 114. A shielded sheath 2812 of the same construction as the prior embodiments discussed herein is positioned over the lead body of the paddle lead 2802.

Figure 28:
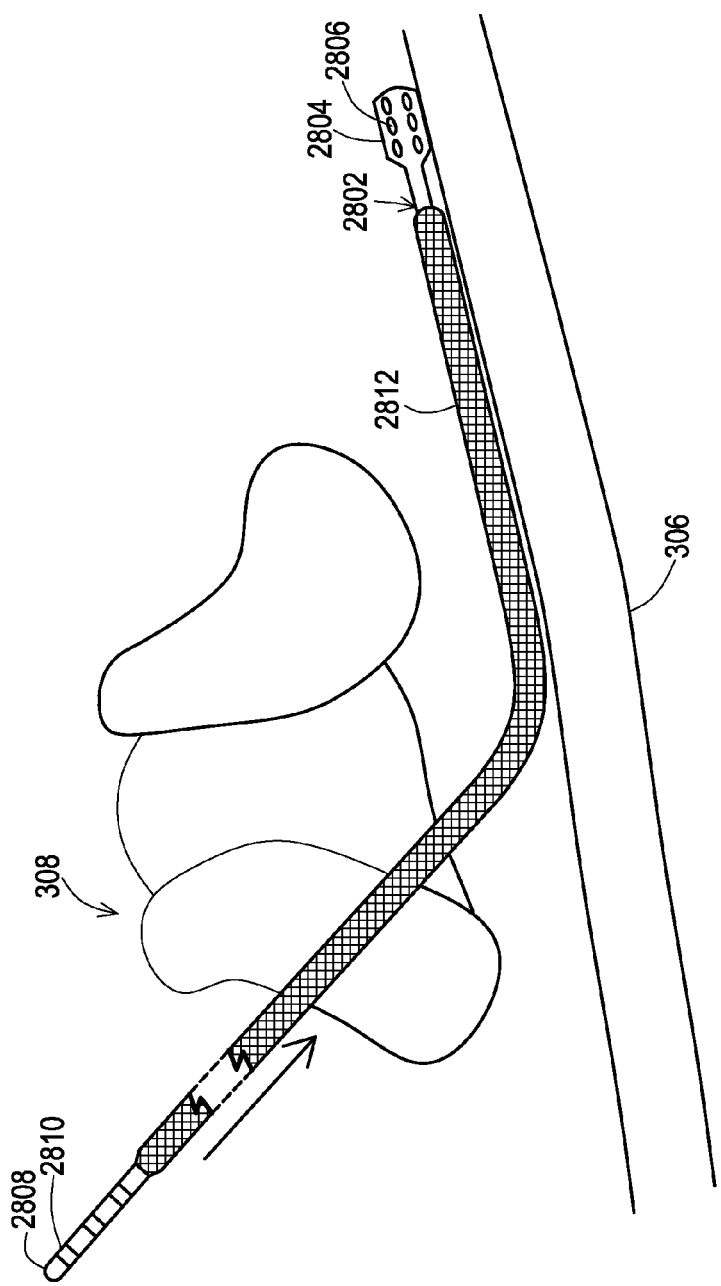
FIG. 28 shows the shielded sheath positioned over the paddle lead and being positioned within the epidural space.

As can be seen in FIG. 27 as well as in FIG. 28, the inside diameter of the shielded sheath 2812 is large enough to fit over the lead body. However, the width of the paddle portion 2804 is larger than the inside diameter of the shielded sheath 2812, which confines the position of the shielded sheath 2812 on the lead 2802. FIG. 28 further shows that the paddle lead 2802 and the shielded sheath 2812 are positioned within the epidural space by passing through the spinal structures 308 which may be further manipulated surgically when introducing the paddle portion 2804. Where the shielded sheath 2812 is being installed at the time of implantation of the lead 2802, various procedures are possible as discussed with reference to FIGS. 29 and 30. Where the lead 2802 is already implanted, then the shielded sheath 2812 may be added such as by a procedure shown in FIG. 31.

Figure 29:
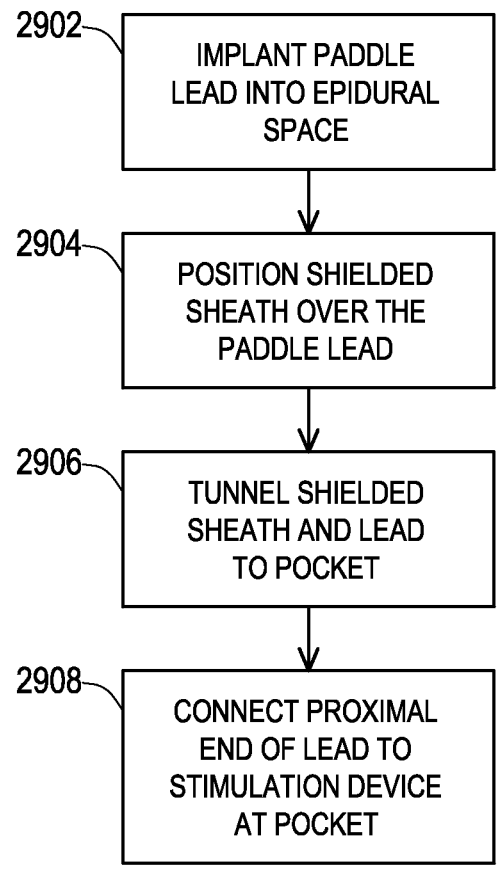
FIG. 29 shows a set of operations for one manner of implanting a shielded sheath and an implantable medical paddle lead.

The procedure of FIG. 29 begins by the paddle lead 2802 being implanted into the epidural space to place the paddle portion 2804 at the target site at operation 2902. The shielded sheath 2812 is then positioned over the paddle lead 2802 by feeding the proximal end of the paddle lead 2802 into the distal end of the shielded sheath and advancing the shielded sheath 2812 into the epidural space toward the paddle portion 2804 while the position of the lead 2802 is maintained at an operation 2904. Once the shielded sheath 2812 has been fully advanced onto the lead 2802, it may be desirable in some instances to also create a strain relief loop in the combination of the paddle lead 2802 and attached sheath 2812, such that the strain relief loop is shielded, at this intermediate location in the body of the patient near the entry to the epidural space. The proximal end of the lead 2802 and the shielded sheath 2812 positioned on the lead 2802 are then tunneled to the pocket 114 at an operation 2906. The proximal end 2808 of the lead 2802, which includes contacts 2810, is then connected to the stimulation device 2702 at an operation 2908. It may also be desirable in some instances to create a strain relief loop in the combination of the paddle lead 2802 and attached sheath 2812, such that the strain relief loop is shielded, at this location near the pocket 114 prior to connecting the proximal end 2808 to the device 2702.

An alternative procedure as shown in FIG. 30 begins by the shielded sheath 2812 being positioned over the paddle lead 2802. The proximal end of the paddle lead 2802 is fed into the distal end of the shielded sheath, and the shielded sheath 2812 is advanced toward the paddle portion 2804 prior to implantation of the lead 2802 at an operation 3002. The paddle lead 2802 and shielded sheath 218 are then implanted into the epidural space to place the paddle portion 2804 at the target site at operation 2902 at an operation 3004. With the shielded sheath 2812 fully advanced onto the lead 2802 and the combination of the shielded sheath 2812 and lead 2802 having been fully advanced to the stimulation site within the epidural space, it may be desirable in some instances to also create a strain relief loop in the combination of the paddle lead 2802 and attached sheath 2812, such that the strain relief loop is shielded, at this intermediate location in the body of the patient near the entry to the epidural space. The proximal end of the lead 2802 and the shielded sheath 2812 positioned on the lead 2802 are then tunneled to the pocket 114 at an operation 3006. The proximal end 2808 of the lead 2802, which includes contacts 2810, is then connected to the stimulation device 2702 at an operation 3008. It may also be desirable in some instances to create a strain relief loop in the combination of the paddle lead 2802 and attached sheath 2812, such that the strain relief loop is shielded, at this location near the pocket 114 prior to connecting the proximal end 2808 to the device 2702.

Figure 31B:
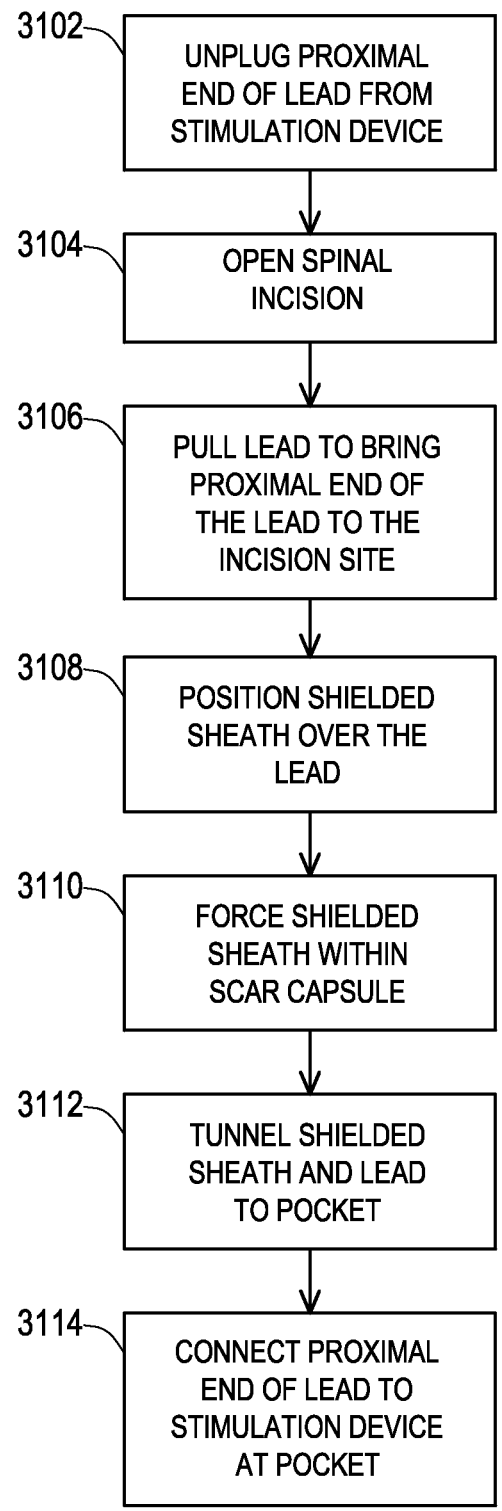

The procedures of FIG. 31A or 31B may be used to retrofit an implanted paddle lead 2802 with a shielded sheath 2812. The example of FIG. 31A may be implemented when a strain relief loop is either not already present or is present but not fibrosed and a strain relief loop is not desired upon placing the shielded sheath 2812 onto the lead 2802. This procedure begins by unplugging the proximal end 2808 of the lead 2802 from the stimulation device 2702 at an operation 3101. If there is a strain relief loop that is present but not fibrosed, then the lead may be gently pulled in the proximal direction to straighten the existing strain relief loop. The shielded sheath 2812 is then positioned over the paddle lead 2802 by feeding the exposed proximal end of the paddle lead 2802 into the distal end of the shielded sheath 2812 and advancing the shielded sheath 2812 into the epidural space toward the paddle portion 2804 while the position of the lead 2802 is maintained at an operation 3103. The shielded sheath 2812 may be forced into a scar capsule that has formed around the distal area of the lead present in the epidural space in order to fully advance the shielded sheath 2812 to the paddle portion 2804 at an operation 3105. The proximal end 2808 of the lead 2802, which includes contacts 2810, is then connected to the stimulation device 2702 at an operation 3107.

The example of FIG. 31B may be implemented when one or more strain relief loops are already present and fibrosed and/or are desired upon placing the shielded sheath 2812 onto the lead 2802. This procedure begins by unplugging the proximal end 2808 of the lead 2802 from the stimulation device 2702 at an operation 3102. The point of entry 2704, typically a surgical incision, of the lead 2802 into the epidural space may be reopened to access the lead 2802 at an operation 3104. The lead 2802 is then pulled from the pocket 114 to the point of entry 2704 to pull any existing strain relief loop straight and to gain access to the proximal end of the lead 2802 at an operation 3106. The shielded sheath 2812 is then positioned over the paddle lead 2802 by feeding the exposed proximal end of the paddle lead 2802 into the distal end of the shielded sheath and advancing the shielded sheath 2812 into the epidural space toward the paddle portion 2804 while the position of the lead 2802 is maintained at an operation 3108. The shielded sheath 2812 may be forced into a scar capsule that has formed around the distal area of the lead present in the epidural space in order to fully advance the shielded sheath 2812 to the paddle portion 2804 at an operation 3110. With the shielded sheath 2812 fully advanced onto the lead 2802, it may be desirable in some instances to also create a strain relief loop in the combination of the paddle lead 2802 and attached sheath 2812, such that the strain relief loop is shielded, at this intermediate location in the body of the patient near the entry to the epidural space. The proximal end of the lead 2802 and the shielded sheath 2812 positioned on the lead 2802 are then tunneled to the pocket 114 at an operation 3112. The proximal end 2808 of the lead 2802, which includes contacts 2810, is then connected to the stimulation device 2702 at an operation 3114. It may also be desirable in some instances to create a strain relief loop in the combination of the paddle lead 2802 and attached sheath 2812, such that the strain relief loop is shielded, at this location near the pocket 114 prior to connecting the proximal end 2808 to the device 2702.

Figure 32:
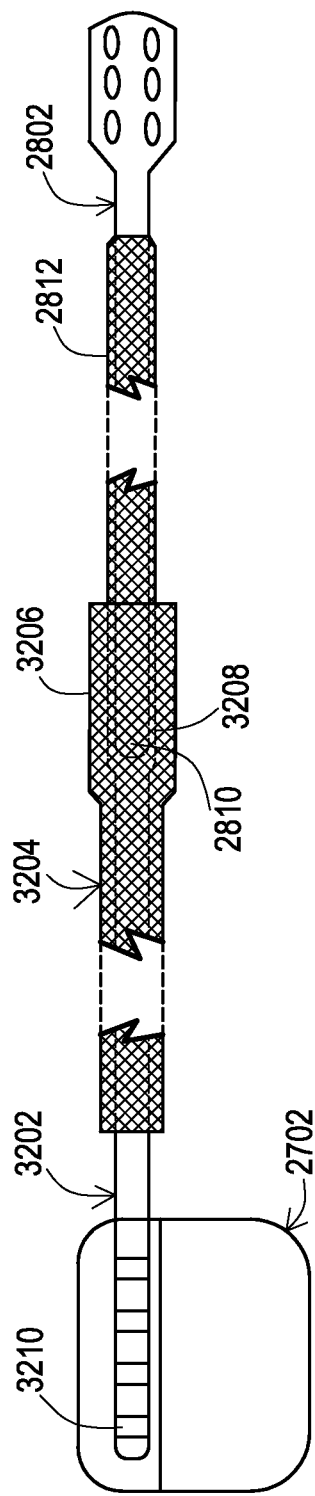
FIG. 32 shows an example of an implantable medical system that includes a lead extension, a paddle lead, and first and second shielded sheaths for the paddle lead and lead extension.

Should the paddle lead 2802 require an extension to reach the target site, FIG. 32 shows an example of such a configuration. Here, the proximal end 2810 of the lead 2802 has been connected to a distal connector block 3208 of connectors of a lead extension 3202. The shielded sheath 2812 is present on the lead 2802 while a second shielded sheath 3204 is present on the lead extension 3202. The second shielded sheath 3204 includes a portion 3206 that covers the distal connector block 3208 of the extension 3202. The proximal end of the lead 2802 includes contacts 3210 that are plugged into the stimulation device 2702.

The shielded sheath 2812 of FIGS. 27, 28, and 32 as well as the second shielded sheath 3204 may also include an electrical contact, such as the contact 2406 in FIG. 24, on the proximal end that can then establish a ground path with the stimulation device 2702. As another example, the electrical contact of the shielded sheath 2812 or second shielded sheath 3204 may have a first portion with a first diameter and a second portion and a second diameter that is smaller than the first, as shown in FIG. 25.

While embodiments have been particularly shown and described, it will be understood by those skilled in the art that various other changes in the form and details may be made therein without departing from the spirit and scope of the invention.

What is claimed is:

1. An apparatus comprising:
    an implantable medical lead having a most distal proximal contact and a most proximal distal electrode;
    a sheath containing a shield layer positioned about the implantable medical lead between the most distal proximal contact and the most proximal distal electrode, the sheath having an outer diameter greater than an outer diameter of the proximal contact and the distal electrode, the sheath also having a proximal end positioned distally of the most distal proximal contact and having a distal end positioned proximally of the most proximal distal electrode; and
    an anchoring structure holding the sheath in a fixed position about the implantable medical lead, the anchoring structure comprising a sleeve positioned around an exterior circumference of the sheath so as to overlap a point where the lead exits the sheath to partially directly engage the lead and partially directly engage the sheath and a suture wrapped around an exterior circumference of the sleeve.

2. The apparatus of claim 1, wherein the shield layer comprises braided wires.

3. The apparatus of claim 1, wherein the shield layer is encapsulated within a polymer of the sheath.

4. The apparatus of claim 1, further comprising an electrical contact on the proximal end of the sheath in electrical contact with the shield layer.

5. The apparatus of claim 4, wherein the electrical contact has a first portion with a first diameter and a second portion with a second diameter that is smaller than the first diameter.

6. An implantable medical system, comprising:
an implantable stimulation device;
an implantable medical lead having a most distal proximal contact and a most proximal distal electrode with the most distal proximal contact being electrically coupled to the implantable stimulation device;
a sheath containing a shield layer positioned about the implantable medical lead between the proximal contact and the distal electrode, the sheath having an outer diameter greater than an outer diameter of the proximal contact and the distal electrode, the sheath also having a proximal end positioned distally of the most distal proximal contact and having a distal end positioned proximally of the most proximal distal electrode; and
an anchoring structure holding the sheath in a fixed position about the implantable medical lead, the anchoring structure comprising a sleeve positioned around an exterior circumference of the sheath so as to overlap a point where the lead exits the sheath to partially directly engage the lead and partially directly engage the sheath and a suture wrapped around an exterior circumference of the sleeve.

7. The system of claim 6, wherein the shield layer comprises braided wires.

8. The system of claim 6, wherein the shield layer is encapsulated within a polymer of the sheath.

9. The system of claim 6, wherein the implantable medical lead is physically coupled directly to the implantable stimulation device.

10. The system of claim 6, further comprising:
an implantable medical lead extension having a proximal contact and a distal connector block, a second sheath containing a shield layer positioned about the implantable medical lead extension between the proximal contact and a distal end of the implantable medical lead extension, wherein the proximal contact of the implantable medical lead is directly coupled to the distal connector block and wherein the proximal contact of the implantable medical lead extension is directly coupled to the implantable stimulation device; and
an anchoring structure holding the second sheath in a fixed position about the implantable medical lead extension.

11. The system of claim 6, wherein at least one end of the sheath includes a tapered edge.

12. The apparatus of claim 1, wherein at least one end of the sheath includes a tapered edge.

* * * * *